(12) United States Patent
Stephen et al.

(10) Patent No.: US 8,753,851 B2
(45) Date of Patent: Jun. 17, 2014

(54) SYSTEMS AND METHODS FOR CULTURING ALGAE WITH BIVALVES

(75) Inventors: David Stephen, Davis, CA (US); Gaye Elizabeth Morgenthaler, Woodside, CA (US); Benjamin Chiau-pin Wu, San Ramon, CA (US); David Vancott Jones, Woodside, CA (US)

(73) Assignee: LiveFuels, Inc., Menlo Park, CA (US)

( * ) Notice: Subject to any disclaimer, the term of this patent is extended or adjusted under 35 U.S.C. 154(b) by 0 days.

(21) Appl. No.: 13/263,980

(22) PCT Filed: Apr. 16, 2010

(86) PCT No.: PCT/US2010/031340
§ 371 (c)(1),
(2), (4) Date: Dec. 19, 2011

(87) PCT Pub. No.: WO2010/121094
PCT Pub. Date: Oct. 21, 2010

(65) Prior Publication Data
US 2012/0231513 A1 Sep. 13, 2012

Related U.S. Application Data

(63) Continuation of application No. 13/263,980, filed as application No. PCT/US2010/031340 on Apr. 16, 2010.

(60) Provisional application No. 61/170,524, filed on Apr. 17, 2009.

(51) Int. Cl.
*C12P 7/64* (2006.01)
*C12N 1/12* (2006.01)
*C12M 1/00* (2006.01)
*A01K 61/00* (2006.01)
*C11B 1/10* (2006.01)

(52) U.S. Cl.
USPC ............... 435/134; 435/257.1; 435/289.1; 554/8; 119/242

(58) Field of Classification Search
None
See application file for complete search history.

(56) References Cited

U.S. PATENT DOCUMENTS

| 972,175 A | 10/1910 | Evans |
| 2,637,978 A | 5/1953 | Evans et al. |

(Continued)

FOREIGN PATENT DOCUMENTS

| DE | 101 43 793 A1 | 5/2002 |
| JP | 05-244966 | 9/1993 |

(Continued)

OTHER PUBLICATIONS

Grant, The relationship of bioenergetics and the environment to the field of cultured bivalves, Journal of Experimental Marine Biology and Ecology, 200 (1996) 239-256.*

(Continued)

*Primary Examiner* — Karen Cochrane Carlson
*Assistant Examiner* — Jennifer M. H. Tichy
(74) *Attorney, Agent, or Firm* — Squire Sanders (US) LLP

(57) ABSTRACT

Provided herein are systems and methods for extracting lipids and/or producing biofuel from algae in marine and freshwater environments, wherein algae and bivalves are co-cultured in a system of enclosures comprising water that comprises recycled nutrients that are essential for algal growth. The system also include enclosures for culturing fishes which are used to harvest the algae.

22 Claims, 2 Drawing Sheets

(56) References Cited

U.S. PATENT DOCUMENTS

| | | |
|---|---|---|
| 2,653,451 A | 9/1953 | McCullough |
| 2,927,435 A | 3/1960 | Upson |
| 3,155,609 A | 11/1964 | Pampel |
| 3,473,509 A | 10/1969 | Miyamura |
| 3,499,421 A | 3/1970 | MacDonald et al. |
| 3,683,627 A | 8/1972 | Girden |
| 3,811,411 A | 5/1974 | Moeller |
| 3,815,546 A | 6/1974 | Plante |
| 4,044,720 A | 8/1977 | Fast |
| 4,055,145 A | 10/1977 | Mager et al. |
| 4,080,795 A | 3/1978 | Weidler, Jr. |
| RE30,038 E | 6/1979 | Sweeney |
| 4,189,379 A | 2/1980 | Finley |
| 4,231,312 A | 11/1980 | Person |
| 4,281,614 A | 8/1981 | McNary et al. |
| 4,337,727 A | 7/1982 | Mickelsen et al. |
| 4,368,691 A | 1/1983 | Brune |
| 4,428,702 A | 1/1984 | Abbott et al. |
| 4,543,190 A | 9/1985 | Modell |
| 4,557,629 A | 12/1985 | Meek et al. |
| 4,597,360 A | 7/1986 | Johnson |
| 4,599,014 A | 7/1986 | McGillivray et al. |
| 4,687,380 A | 8/1987 | Meek et al. |
| 4,696,603 A | 9/1987 | Danaczko et al. |
| 4,724,086 A | 2/1988 | Kortmann |
| 4,810,135 A | 3/1989 | Davenport et al. |
| 4,818,145 A | 4/1989 | Carruba |
| 4,896,626 A | 1/1990 | Holt et al. |
| 4,979,871 A | 12/1990 | Reiner |
| 5,040,486 A | 8/1991 | Pack |
| 5,106,230 A | 4/1992 | Finley |
| 5,267,812 A | 12/1993 | Suzuki et al. |
| 5,299,530 A | 4/1994 | Mukadam et al. |
| 5,338,673 A | 8/1994 | Thepenier et al. |
| 5,359,962 A | 11/1994 | Loverich |
| 5,377,624 A | 1/1995 | Craig et al. |
| 5,438,958 A | 8/1995 | Ericsson et al. |
| 5,439,060 A | 8/1995 | Huete et al. |
| 5,511,514 A | 4/1996 | Hitchins et al. |
| 5,539,133 A | 7/1996 | Kohn et al. |
| 5,545,808 A | 8/1996 | Hew et al. |
| 5,582,691 A | 12/1996 | Flynn et al. |
| 5,588,781 A | 12/1996 | Smolinski et al. |
| 5,596,947 A | 1/1997 | Creppel et al. |
| 5,628,279 A | 5/1997 | Bones, IV |
| 5,642,966 A | 7/1997 | Morrison et al. |
| 5,713,303 A | 2/1998 | Willinsky et al. |
| 5,778,823 A | 7/1998 | Adey et al. |
| 5,820,759 A | 10/1998 | Stewart et al. |
| 5,836,266 A | 11/1998 | Watanabe |
| 5,945,318 A | 8/1999 | Breivik et al. |
| 5,992,089 A | 11/1999 | Jones et al. |
| 5,998,698 A | 12/1999 | Cooper et al. |
| 6,000,551 A | 12/1999 | Kanel et al. |
| 6,015,713 A | 1/2000 | Wright, Jr. et al. |
| 6,027,286 A | 2/2000 | Pollack |
| 6,056,919 A | 5/2000 | Markels, Jr. |
| 6,065,245 A | 5/2000 | Seawright |
| 6,111,166 A | 8/2000 | Van de Winkel |
| 6,180,845 B1 | 1/2001 | Catallo et al. |
| 6,190,715 B1 | 2/2001 | Crowther et al. |
| 6,192,833 B1 | 2/2001 | Brune et al. |
| 6,216,635 B1 | 4/2001 | McRobert |
| 6,313,545 B1 | 11/2001 | Finley et al. |
| 6,350,890 B1 | 2/2002 | Kiy et al. |
| 6,391,201 B1 | 5/2002 | Pelz |
| 6,509,178 B1 | 1/2003 | Tanaka et al. |
| 6,607,900 B2 | 8/2003 | Bailey et al. |
| 6,615,767 B1 | 9/2003 | Untermeyer et al. |
| 6,750,048 B2 | 6/2004 | Ruecker et al. |
| 6,800,299 B1 | 10/2004 | Beaudoin et al. |
| 6,821,413 B1 | 11/2004 | Alkhalidl |
| 6,863,027 B1 | 3/2005 | Silva |
| 6,986,323 B2 | 1/2006 | Ayers |
| 7,126,235 B2 | 10/2006 | Bernhoff et al. |
| 7,258,790 B2 | 8/2007 | Brune et al. |
| 7,329,099 B2 | 2/2008 | Hartman |
| 7,347,667 B2 | 3/2008 | Wobben |
| 7,351,558 B2 | 4/2008 | Ruecker et al. |
| 7,662,598 B2 | 2/2010 | Ruecker et al. |
| 7,678,171 B2 | 3/2010 | Beckley et al. |
| 7,678,931 B2 | 3/2010 | Fichtali et al. |
| 7,887,694 B2 | 2/2011 | Constantz et al. |
| 2002/0072109 A1 | 6/2002 | Bayless et al. |
| 2002/0110582 A1 | 8/2002 | Place et al. |
| 2002/0151463 A1 | 10/2002 | Woychik et al. |
| 2003/0124218 A1 | 7/2003 | Hjaltason et al. |
| 2003/0154926 A1 | 8/2003 | Untermeyer et al. |
| 2003/0221361 A1 | 12/2003 | Russell et al. |
| 2004/0074760 A1 | 4/2004 | Portnoff et al. |
| 2004/0089592 A1 | 5/2004 | Shechter et al. |
| 2004/0107914 A1 | 6/2004 | Untermeyer et al. |
| 2004/0262980 A1 | 12/2004 | Watson |
| 2005/0115893 A1 | 6/2005 | Brune et al. |
| 2005/0164333 A1 | 7/2005 | Vincent |
| 2005/0170479 A1 | 8/2005 | Weaver et al. |
| 2005/0218071 A1 | 10/2005 | Austin et al. |
| 2005/0260553 A1 | 11/2005 | Berzin |
| 2006/0016760 A1 | 1/2006 | Bozak et al. |
| 2006/0169216 A1 | 8/2006 | Shields et al. |
| 2006/0229222 A1 | 10/2006 | Muller et al. |
| 2006/0254134 A1 | 11/2006 | Levy |
| 2007/0010682 A1 | 1/2007 | Myllyoja et al. |
| 2007/0033863 A1 | 2/2007 | Butler |
| 2007/0048848 A1 | 3/2007 | Sears |
| 2007/0082399 A1 | 4/2007 | Egorova-Zachernyuk |
| 2007/0092962 A1 | 4/2007 | Sheppard |
| 2007/0113467 A1 | 5/2007 | Abou-Nemeh |
| 2007/0131579 A1 | 6/2007 | Koivusalmi et al. |
| 2007/0135316 A1 | 6/2007 | Koivusalmi et al. |
| 2007/0135663 A1 | 6/2007 | Aalto et al. |
| 2007/0135666 A1 | 6/2007 | Koivusalmi et al. |
| 2007/0135669 A1 | 6/2007 | Koivusalmi et al. |
| 2007/0151522 A1 | 7/2007 | Brauman |
| 2007/0166411 A1* | 7/2007 | Anthony et al. ............... 424/750 |
| 2007/0202582 A1 | 8/2007 | Bush et al. |
| 2007/0274952 A1 | 11/2007 | Kang |
| 2007/0281883 A1 | 12/2007 | Rosenfeld et al. |
| 2007/0298156 A1* | 12/2007 | Mehansho et al. ............ 426/590 |
| 2007/0299291 A1 | 12/2007 | Koivusalmi |
| 2008/0009055 A1 | 1/2008 | Lewnard |
| 2008/0020097 A1 | 1/2008 | Torp et al. |
| 2008/0092436 A1 | 4/2008 | Seames et al. |
| 2008/0138867 A1 | 6/2008 | Dayton et al. |
| 2008/0155888 A1 | 7/2008 | Vick et al. |
| 2008/0160593 A1 | 7/2008 | Oyler |
| 2008/0166779 A1 | 7/2008 | Thomas et al. |
| 2008/0188676 A1 | 8/2008 | Anderson et al. |
| 2008/0299643 A1 | 12/2008 | Howard et al. |
| 2008/0320610 A1 | 12/2008 | Yoshizaki et al. |
| 2009/0077863 A1 | 3/2009 | Oyler |
| 2009/0077864 A1 | 3/2009 | Marker et al. |
| 2009/0081748 A1 | 3/2009 | Oyler |
| 2009/0158638 A1 | 6/2009 | Hatcher et al. |
| 2010/0049673 A1 | 2/2010 | Millen, II et al. |
| 2010/0050502 A1 | 3/2010 | Wu et al. |
| 2010/0077654 A1 | 4/2010 | Wu et al. |
| 2010/0081835 A1 | 4/2010 | Wu et al. |
| 2010/0236137 A1 | 9/2010 | Wu et al. |
| 2011/0010987 A1 | 1/2011 | Knottenbelt et al. |
| 2011/0239318 A1 | 9/2011 | Stephen et al. |
| 2012/0058248 A1 | 3/2012 | Stephen et al. |
| 2012/0058542 A1 | 3/2012 | Wu et al. |
| 2012/0283458 A1 | 11/2012 | Morgenthaler et al. |
| 2012/0284165 A1 | 11/2012 | Morgenthaler et al. |
| 2012/0285392 A1 | 11/2012 | Morgenthaler et al. |

FOREIGN PATENT DOCUMENTS

| | | |
|---|---|---|
| JP | 3644842 | 5/2005 |
| JP | 2007054027 | 3/2007 |
| JP | 2008-212772 | 9/2008 |
| WO | WO 99/31963 | 7/1999 |
| WO | WO 01/54510 A1 | 8/2001 |

(56) References Cited

FOREIGN PATENT DOCUMENTS

| WO | WO 2004/068941 A1 | 8/2004 |
|---|---|---|
| WO | WO 2004/070165 A1 | 8/2004 |
| WO | WO 2004/082399 A2 | 9/2004 |
| WO | WO 2008/013548 | 1/2008 |
| WO | WO 2008/048861 | 4/2008 |
| WO | WO 2008/083352 | 7/2008 |
| WO | WO 2008/105649 | 9/2008 |
| WO | WO 2010/021753 | 2/2010 |
| WO | WO 2010/036333 | 4/2010 |
| WO | WO 2010/036334 | 4/2010 |
| WO | WO 2010/059598 | 5/2010 |
| WO | WO 2010/077922 | 7/2010 |
| WO | WO 2010/104908 | 9/2010 |
| WO | WO 2010/121094 | 10/2010 |
| WO | WO 2010/132628 | 11/2010 |
| WO | WO 2010/141794 | 12/2010 |
| WO | WO-2010/147955 | 12/2010 |
| WO | WO-2011/008900 | 1/2011 |
| WO | WO-2011/119677 | 9/2011 |

OTHER PUBLICATIONS

Garrison et al., Fishing effects on spatial distribution and trophic guild structure of the fish community in the Georges Bank region, ICES Journal of Marine Science, 57: 723-730 (2000).*
Albers et al., "Short Path Distillation in the Fish Oil Industry," UIC GmbH, 2006.
Barnabe, "Harvesting Micro-Algae," pp. 207-212 in *Aquaculture*, vol. 1, Barnabe, G. (ed), 1990, Ellis Horwood, New York.
Becker, "Large-Scale Cultivation," Chapter 10 in *Microalgae Biotechnology and Microbiology*, 1994, Cambridge University Press, pp. 63-171.
Becker, "Microalgae for Aquaculture: The Nutritional Value of Microalgae for Acquaculture," *Handbook of Microalgal Culture: Biotechnology and Applied Phycology*, Richmond (ed)., 2004, Wiley-Blackwell, pp. 380-391.
Belarbi et al., "A Process for High Yield and Scaleable Recovery of High Purity Eicosapentacnoic Acid Esters from Microalgae and Fish Oil," *Enzyme and Microbial Technology*, 26 (2000): 516-529.
Berger et al., "Increase of Carbon Dioxide in the Atmosphere During Deglaciation: The Coral Reef Hypothesis," *Naturwissenschaften*, 69 (1982): 87-88.
Bligh et al., "A Rapid Method of Total Lipid Extraction and Purification," *Canadian J. Biochem. Physiol.*, 37 (1959): 911-917.
Boucher et al., "In situ Measurement of Respiratory Metabolism and Nitrogen Fluxes at the Interface of Oyster Beds," *Mar. Ecol. Prog. Ser.*, 1988, 44: 229-238.
Bridgwater, "Biomass Fast Pyrolysis," *Thermal Science*, 2004, 8(2): 21-49.
Browdy et al., "Comparison of Pond Production Efficiency, Fatty Acid Profiles, and Contaminants in *Litopenaeus vannamei* Fed Organic Plant-based and Fish-meal-based Diets," *J. World Aquaculture Soc.*, 2006, 37(4), 437-451.
Brune et al., "Intensification of Pond Aquaculture and High rate Photosynthetic Systems," *Aquaculture Eng 'g*, 2003, 28: 65-86.
Chauvaud et al., "Clams as $CO_2$ Generators: The *Potamocorbula amurensis* Example in San Francisco Bay," *Limnol. Oceanogr.*, 2003, 48(6): 2086-2092.
Chiaramonti et al., "Power Generation Using Fast Pyrolysis Liquids from Biomass," *Renewable and Sustainable Energy Reviews*, Aug. 2007, 11(6), pp. 1056-1086.
Chisti, "Biodiesel from Microalgae," *Biotechnology Advances*, 25 (2007), pp. 294-306.
Cho, "Feeding Systems for Rainbow Trout and other Salmonids with Reference to Current Estimates of Energy and Protein Requirements," *Aquaculture*, 100 (1992), 107-123.
Csordas et al., "An Integrated Photobioreactor and Foam Fractionation Unit for the Growth and Harvest of *Chaetoceros* spp. in Open Systems," *Aquacultural Engineering*, 30 (2004), pp. 15-30.

Czernik et al., "Overview of Applications of Biomass Fast Pyrolysis Oil," *Energy & Fuels*, 2004, 18, pp. 590-598.
Durbin et al., "Grazing Rates of the Atlantic Menhaden *Brevoortia tyrannus* as a Function of Particle Size and Concentration," *Marine Biology*, 1975, 33: 265-277.
Faludi, "Fish for Fuel," *WorldChanging*, 2008, available at http://www.worldchanging.com/archives/007497.html (last visited Jun. 30, 2008).
Fox, "Intensive Algal Culture Techniques," *CRC Handbook of Mariculture*, vol. 1, McVey, JP (ed), CRC Press, Florida, (1983) pp. 15-41.
Franklin, H. Bruce, "The Most Important Fish in the Sea," *Discovery*, Sep. 2001: 44-51.
Frey et al., "Effects of micro-nutrients and major nutrients on natural phytoplankton populations," *J. of Plankton Research*, 2 (1980): 1-22.
Gjedrem, "Genetic Variation in Quantitative Traits and Selective Breeding in Fish and Shellfish," *Aquaculture*, 33 (1983): 51-72.
Gnansounou et al., "Ethanol Fuel from Biomass: A Review," *J. Scientific & Industrial Res.*, 64, (Nov. 2005): 809-821.
Gold, "Biofuel Bet Aims to Harvest Fish that Feed on Algae," *Wall Street Journal (online)*, (Aug. 18, 2009), available at http://online.wsj.com/article/SB125055779852138901.html.
Grima et al., "Downstream Processing of Cell-Mass and Products," Chapter 10 in *Handbook of Microalgal Culture: Biotechnology and Applied Phycology*, 2004, Richmond (ed)., Wiley-Blackwell, p. 215-252.
Hara et al., "Lipid Extraction of Tissues with a Low-Toxicity Solvent," *Anal. Biochem.*, 90 (1978): 420-426.
Hussenot, "Emerging Effluent Management Strategies in Marine Fish-Culture Farms Located in European Coastal Wetlands," *Aquaculture*, 226 (2003), pp. 113-128.
Irwin et al., "Scaling-up From Nutrient Physiology to the Size-Structure of Phytoplankton Communities," *J. of Plankton Research*, 28 (2006): 1-13.
Jørgenson, "Bivalve Filter Feeding Revisited," *Mar. Ecol. Prog. Ser.*, 142 (1996): 287-302.
Kemmerer, "Environmental Preferences and Behavior Patterns of Gulf Menhaden (*Brevoortia patron*) Inferred from Fishing and Remotely Sensed Data," *Conference on the Physiological and Behavioral Manipulation of Food Fish as Production and Management Tools*, Bellagio, Italy, Nov. 3-8, 1977, printed on pp. 345-370 in *Fish Behavior and Its Use in the Capture and Culture of Fishes*, edited by Bardach et al., Manila: International Center for Living Aquatic Resources Management (1980).
Kusdiana et al., "Effects of Water on Biodiesel Fuel Production by Supercritical Methanol Treatment," *Bioresource Technology*, 91 (2004), 289-295.
Kusdiana et al., "Kinetics of Transesterification in Rapeseed Oil to Biodiesel Fuel as Treated in Supercritical Methanol," *Fuel*, 80 (2001), 693-698.
Latour et al., "Toward Ecosystem-Based Fisheries Management: Strategies for Multispecies Modeling and Associated Data Requirements," *Fisheries*, 28 (2003):10-22.
Leaver et al., "Towards Fish Lipid Nutrigenomics: Current State and Prospects for Fin-Fish Aquaculture," *REviews in Fisheries Science*, 16(S1): (2008): 71-92.
Lefebvre et al., "Outdoor Phytoplankton Continuous Culture in a Marine Fish-Phytoplankton-Bivalve Integrated System: Combined Effects of Dilution Rate and Ambient Conditions on Growth Rate, Biomass and Nutrient Cycling," *Aquaculture*, 240 (2004): 211-231.
Levin et al., "Harvesting of Algae by Froth Flotation," *Resource Research, Inc.*, 10 (1961): 169-175.
Li et al., "Biofuels from Microalgae," *Biotechnol. Progress*, (2008): 815-820.
McGinnis et al., "Characterization of the Growth and Lipid Content of the Diatom *Chaetoceros muelleri*," *J. Appl. Phycology*, 9 (1997): 19-24.
Neori et al., "Integrated Aquaculture: Rationale, Evolution and State of the Art Emphasizing Seaweed Biofiltration in Modern Mariculture," *Aquaculture*, 231 (2004): 361-391.
Newell, "Ecosystem Influences of Natural and Cultivated Populations of Suspension-Feeding Bivalve Molluscs: A Review," *J. Shellfish Res.*, 23 (2004): 51-61.

(56) References Cited

OTHER PUBLICATIONS

Oasmaa et al, "Fuel Oil Quality of Biomass Pyrolysis Oils—State of the Art for End Users," *Energy & Fuels*, 13 (1999): 914-921.
Patent Cooperation Treaty, International Search Report for PCT/US2010/031340, mailed Jun. 29, 2010.
Patent Cooperation Treaty, Written Opinion of the International Searching Authority for PCT/US2010/031340, mailed Jun. 29, 2010.
Peck, "On the Food of the Menhaden," *Bull. U.S. Fish. Comm.* 13 (1893): 113-126, plus 8 pages of illustrations on unnumbered pages.
Piccolo, "Aquatic Biofuels," available at http://km.fao.org/fileadmin/user_upload/fsn/docs/Microsoft%20Word%20-%20Aquaticbiofuels.pdf (May 2008).
Piccolo, "Aquatic Biofuels New Options for Bioenergy," Thesis Topic for a MBA, University of Malta, Rome Campus, available at http://www.scribd.com/doc/5598814/aquaticbiofuelpresweb (undated).
Powell et al., "Early Life History of Atlantic Menhaden *Brevoortia tyrannus*, and Gulf Menhaden, *B. patronus*," *Fishery Bulletin*, 84 (1986): 991-994.
Saka et al., "Biodiesel Fuel from Rapeseed Oil as Prepared in Supercritical Methanol," *Fuel*, 80 (2001): 225-231.
Sheehan et al. "A Look Back at the U.S. Department of Energy's Aquatic Species Program: Biodiesel from Algae," National Renewable Energy Laboratory, (1998): 1-294.
Shimeno et al., "Metabolic Response to Feeding Rates in Common Carp, *Cyprinus carpio*," *Aquaculture*, 151 (1997): 371-377.
Spath et al., "Preliminary Screening—Technical and Economic Assessment of Synthesis Gas to Fuels and Chemicals with Emphasis on the Potential for Biomass-derived Syngas," NREL/TP-510-34929 (Dec. 2003).
Spolaore et al., "Commercial Applications of Microalgae," *J. Biosci. and Bioeng.*, 101 (2006): 87-96.
Steigers, "Demonstrating the Use of Fish Oil as Fuel in a Large Stationary Diesel Engine," In: Bechtel PJ, editor, *Advances in Seafood by Products*, conference proceedings, Alaska Sea Grant, Fairbanks, AK. p. 187-2000 (2002).
Stephen, "The Reproductive Biology of the Indian oyster *Crassostrea madrasensis* (Preston) II. Gametogenic Cycle and Biochemical Levels," *Aquaculture*, 21 (1980): 147-153.
Technical Article, "Biofuels from Aquatic Resources: Diesel from Fish Waste, Biofuel from Algae," *Eurolish Magazine*, 1 (Feb. 2009): 46-49.
Tyson et al., "Biomass Oil Analysis: Research Needs and Recommendations," NREL/TP-510-34796, (Jun. 2004).
Ware et al., "Coral reefs: sources or sinks of atmospheric $CO_2$?," *Coral Reefs*, 11 (1991): 127-130.
Wurts, "Sustainable Aquaculture in the Twenty-First Century," *Reviews in Fisheries Science*, 8 (2000): 141-150.
United States Patent and Trademark Office, Office Action issued in related U.S. Appl. No. 12/565,610, mailed on May 27, 2011.
United States Patent and Trademark Office, Office Action issued in related U.S. Appl. No. 12/544,862, mailed on Nov. 17, 2011.
United States Patent and Trademark Office, Office Action issued in related U.S. Appl. No. 12/565,610, mailed on Jan. 26, 2012.
Alpine et al., Trophic Interactions and Direct Physical Effects Control Phytoplankton Biomass and Production in an Estuary (1992) *Limnol. Oceanogr.* 37:946-955.
Arai, Genetic Improvement of Aquaculture Finfish Species by Chromosome Manipulation Techniques in Japan (2001) *Aquaculture* 197:205-228.
Armstrong, Grazing Limitation and Nutrient Limitation in Marine Ecosystems: Steady State Solutions of an Ecosystem Model with Multiple Food Chains (1994) *Limnol. Oceanogr.* 39(3):597-608.
Badylak et al., Spatial and temporal distributions of zooplankton in Tampa Bay, Florida, including observations during a Hab event (2008) *J. Plankton Res.* 30:449-465.
Beardmore et al., Monosex Male Production in Finfish as Exemplified by Tilapia: Applications, Problems, and Prospects (2001) *Aquaculture* 197:283-301.

Benfield et al., RAPID: Research on Automated Plankton Identification (2007) *Oceanography* 20:172-187.
Bricker et al., Effects of Nutrient Enrichment in the Nation's Estuaries: A Decade of Change. *NOAA Coastal Ocean Program Decision Analysis Series No. 26, National Centers for Coastal Ocean Science*, Silver Spring, MD (328 pages); on the web at: http://ccma.nos.noaa.gov/publications/eutroupdate/.
Bruland et al., Iron and Macronutrients in California Coastal Upwelling Regimes: Implications for Diatom Blooms (2001) *Limnol. Oceanogr.* 46:1661-1674.
Brune et al., Improved process for harvest and concentration of algal lipid for biodiesel production, 29th Symposium on Biotechnology for Fuels and Chemicals, Apr. 29-May 2, 2007, Denver CO. Abstract 1 page.
Cerda-Reverter et al., Endogenous Melanocortin Antagonist in Fish: Structure, Brain Mapping, and Regulation by Faster of the Goldfish Agouti-Related Protein Gene (2002) *Endocrinology* 144:4552-4581.
Christie, Preparation of Ester Derivatives of Fatty Acids for Chromatographic Analysis (1993) *Advances in Lipid Methodology—vol. Two* pp. 69-111.
Cloern, Our Evolving Conceptual Model of the Coastal Eutrophication Problem (2001) *Mar Ecol Prog Ser* 210:223-253.
Coastal Response Research Center (2010) Technical Readiness of Ocean Thermal Energy Conversion (OTEC), 246 pages.
Culp et al., High-Frequency Germ-Line Transmission of Plasmid DNA Sequencers Injected into Fertilized Zebrafish Eggs (1991) *Proc. Natl. Acad. Sci USA*, 88:7953-7957.
Danaei et al., The Preventable Causes of Death in the United States: Comparative Risk Assessment of Dietary, Lifestyle, and Metabolic Risk Factors (2009) *PLoS Medicine* 6:1-23.
Davis et al., Real-Time Observation of Taxa-Specitic Plankton Distributions: An Optical Sampling Methods (2004)*Marine Ecology Progress Series* 284:77-96.
Deegan, Changes in Body Composition and Morphology of Young-of-the-Year Gulf Menhaden, *Brevoortia patronus* Goode, in Fourleague Bay, Louisiana (1986) *J of Fish Biology* 29:403-415.
Drapcho et al., The Partitioned Aquaculture System: Impact of Design and Environmental Parameters on Algal Productivity and Photosynthetic Oxygen Production (2000) *Aquacultural Engineering* 21:151-168.
Durbin et al., Grazing Rates of the Atlantic Menhaden *Brevoortia tyrannus* as a Function of Particle Size and Concentration (1975) *Marine Biology* 33:265-277.
Edwards et al., The Harvest of Microalgae from the Effluent of a Sewage Fed High Rate Stabilization Pond by *Tilapia nilotica*—Part 2: Studies of the Fish Pond (1981) *Aquaculture* 23:107-147.
Friedland et al., Formation and Seasonal Evolution of Atlantic Menhaden Juvenile Nurseries in Coastal Estuaries (1996) *Estuaries* 19:105-114.
Friedland et al., Influence of plankton on distribution patterns of the filter-feeder *Brevoortia tyrannus* (Pisces: Clupeidae) (1989) *Mar. Ecol. Prog. Ser.* 54:1-11.
Garrison et al., Fishing effects on spatial distribution and trophic guild structure of the fish community in the Georges Bank region (2000) *ICES Journal of Marine Science* 57:723-730.
Grant, The relationship of bioenergetics and the environment to the field of cultured bivalves (1996) *Journal of Experimental Marine Biology and Ecology* 200:239-256.
Grimes et al., Spatial Distribution and Abundance of Larval and Juvenile Fish, Chlorophyll and Macrozooplankton around the Mississippi River Discharge Plume, and the Role of the Plume in Fish Recruitment (1991) *Mar. Ecol. Prog. Ser.* 75:109-119.
Guan et al., Metabolism traits of 'all-fish' growth hormone transgenic common carp (*Cyprinus carpio* L.) (2008) *Aquaculture* 284:217-223.
Hettler, Artificial Fertilization Among Yellowfin and Gulf Menhaden (*Brevoortia*) and Their Hybrid (1968) *Transactions of Am. Fishers Soc'y* 97:119-123.
Hettler, Transporting Adult Larval Gulf Menhaden and Techniques for Spawning in the Laboratory (1983) *The Progressive Fish-Culturist* 45:45-48.
Hutchins et al., Iron-limited Diatom Growth and Si:N Uptake Ratios in a Coastal Upwelling Regime (1998) *Nature* 393:561-564.

(56) References Cited

OTHER PUBLICATIONS

Inoue et al., Electroporation as a New Technique for Producing Transgenic Fish (1990) *Cell. Differ. Develop.* 29:123-128.
Jiao et al., Microbial production of recalcitrant dissolved organic matter: long-term carbon storage in the global ocean (2010) Nature Reviews Microbiology 8:593-599.
Joseph, Fatty Acid Composition of Commercial Menhaden, *Brevoortia spp.*, Oils, 1982 and 1983 (1985) *Marine Fisheries Review* 47:30-37.
Kadereit et al., Evolutionarily Conserved Gene Family Important for Fat Storage (2008) *PNAS* 105:94-99.
Kaiser et al., The Gulf of Mexico Decommissioning Market (2006) *J. of Constr. Eng'g and Mgmt.* 132:815-26.
Kaiser, Offshore Decommissioning Cost Estimation in the Gulf of Mexico (2006) *J. of Constr. Eng'g and Mgmt.* 132:249-58.
Katija et al., A viscosity-enhanced mechanism for biogenic ocean mixing (2009) *Nature* 460:624-627.
Keller et al., Growth of Juvenile Atlantic Menhaden, *Brevoortia tyrannus* (Pisces: Clupeidae) in MERL Mesocosms: Effects of Eutrophication (1990) *Limnol. Oceanogr.* 35:109-122.
Kilham et al., COMBO: a defined freshwater culture medium for algae and zooplankton (1998) *Hydrobiologia* 377:147-159.
Kurokawa et al., Identification of cDNA Coding for a Homologue to Mammalian Leptin from Pufferfish Takifugu rubripes (2005) *Peptides* 26:745-750.
Kyoto Protocol Reference Manual on Accounting of Emissions and Assigned Amount, United Nations Framework Convention on Climate Change. Nov. 2008.
Lamp, Breathless Coastal Seas: WWF Briefing Paper: Dead Ocean Zones—a Global Problem of the 21. Century (2008) *WWF Germany* pp. 2-19.
Lazzaro et al., Planktivores and Plankton Dynamics: Effects of Fish Biomass and Planktivore Type (1992) *Canadian Journal of Fisheries and Aquatic Sciences* 49:1466-1473.
Lazzaro, A Review of Planktivorous Fishes: Their Evolution, Feeding Behaviours, Selectivities, and Impacts (1987) *Hydrobiologia* 146:97-167.
Lekang, Aquaculture Engineering (2007) Blackwell Publishing Ltd., entire Chapter 8.
Lekang, Aquaculture Engineering (2007) Blackwell Publishing Ltd., entire Chapter 10.
Lekang, Aquaculture Engineering (2007) Blackwell Publishing Ltd., entire Chapter 13.
Lekang, Aquaculture Engineering (2007) Blackwell Publishing Ltd., entire Chapter 14.
Lekang, Aquaculture Engineering (2007) Blackwell Publishing Ltd., entire Chapter 15.
Lekang, Aquaculture Engineering (2007) Blackwell Publishing Ltd., entire Chapter 16.
Lekang, Aquaculture Engineering (2007) Blackwell Publishing Ltd., entire Chapter 17.
Lekang, Aquaculture Engineering (2007) Blackwell Publishing Ltd., entire Chapter 19.
Letisse et al., Enrichment of EPA and DHA from sardine by supercritical fluid extraction without organic modifier. I. Optimization of Extraction Conditions (2006) *J. Supercritical Fluids* 38:27-36 (abstract only).
Lipton, *Pfiesteria's* Economic Impact on Seafood Industry Sales and Recreational Fishing (1999) in Proceedings of the Conference, *Economics of Policy Options for Nutrient Management and Pfiesteria*, Gardner and Koch, editors, College Park: Center for Agricultural and Natural Resource Policy, University of Maryland pp. 35-38.
Lu et al., Harmful Algal Bloom Causitive Collected from Hong Kong Waters (2004) *Hydrobiologia* 512:231-238.
Lu et al., Pantropic Retroviral Vector Integration, Expression, and Germline Transmission in Medaka (*Oryzias latipes*) (1997) *Mol. Mar. Biol. Biotechnol.* 6:289-295.
McGONNELL et al., Fishing for Gene Function—Endocrine Modelling in the Zebrafish (2006) *J. Endocrinol.* 189:425-439.

Metz et al., Molecular Biology and Physiology of the Melanocortin System in Fish: A Review (2006) *Gen Comp Endocrinol.* 148:150-162.
Moloney et al., The Size-Based Dynamics of Plankton Food Webs. I. A Simulation Model of Carbon and Nitrogen Flows (1991) *J. of Plankton Research* 13:1003-1038.
Morrissey, Lipid Content in Troll-caught Albacore Tuna and Correlations with Geographical Location, Physical Measurements and Seasonality (undated) *Jour Aquatic Food Product Technology* 13:41-52.
Mueller et al., Effect of Silver Carp *Hypophthahnichthys molitrix* and Freshwater Mussel *Elliptio complanata* Filtration on the Phytoplankton Community of Partitioned Aquaculture System Units (2004) *J. of the World Aquaculture Soc'y* 35:372-382.
Mueller-Feuga, Microalgae for Aquaculture The Current Global Situation and Future Trends (2004) *Handbook of Microalgal Culture: Biotechnology and Applied Phycology* Richmond (ed) pp. 380-391 Wiley-Blackwell.
Müller et al., Efficient Transient Expression System Based on Square Pulse Electroporation and in vivo Luciferase Assay of Fertilized Fish Eggs (1993) *FEES Letts.* 324:27-32.
Müller et al., Introducing Foreign Genes into Fish Eggs with Electroporated Sperm as a Carrier (1992) *Mol. Mar. Biol. Biotechnol.* 1:276-281.
Murakami et al., Micromachined Electroporation System from Transgenic Fish (1994) *J. Biotechnol.* 34:35-42.
Murashita et al., Production of Recombinant Leptin and its Effects on Food Intake in Rainbow Trout (*Oncorhynchus mykiss*) (2008) *Comp. Biochem. Physiol. B*, 150:377-384.
Needleman et al., A General Method Applicable to the Search for Similarities in the Amino Acid Sequence of Two Proteins (1970) *J. Mol. Biol.* 48:443-453.
Nelson et al., Gastroenteropancreatic Hormones and Metabolism in Fish (2006) *General and Comparative Endocrinology* 148:116-124.
Nishida, Development of the appendicularian *Oikopleura dioica* (2008) *Develop. Growth Differ.* 50:S239-256.
Officer et al., The Possible Importance of Silicon in Marine Eutrophication (1980) *Mar. Ecol. Prog. Ser.* 3:83-91.
Omega Protein Corporation, Product Specifications for Menhaden Fish Oil (May 15, 2008).
Omega Protein Corporation, U.S. SEC Form 10-K Report for Fiscal Year Ending Dec. 31, 2007 (2008).
Ospar Commission, OSPAR Integrated Report 2003 on the Europhication Status (2003) London, UK.
Paerl et al., Chapter 8 in Ecology of Harmful Algae (2006) *Springer Berlin Heidelberg* pp. 95-109.
Pandian et al., Ploidy Induction and Sex Control in Fish (1998) *Hydrobiologia* 384:167-243.
Patil et al., Fatty acid composition of 12 microalgae for possible use in aquaculture feed (2007) *Aquaculture Int* 15:1-9.
Pearson et al., Improved Tools for Biological Sequence Comparison (1988) *Proc. Natl. Acad. Sci. (USA)* 85:2444-2448.
Piferrer, Endocrine Sex Control Strategies for the Feminization of Teleost Fish (2001) *Aquaculture* 197:229-281.
Pillay et al., Reproduction and Genetic Selection (2005) *Aquaculture: Principles and Practices, Blackwell Publishing* pp. 174-196.
Powell, A Comparison of Early-Life-History Traits in Atlantic Menhaden *Brevoortia tyrannus* and Gulf Menhaden *B. patronus* (1993) *Fishery Bulletin* 91:119-128.
Quinlan et al., From Spawning Grounds to the Estuary: Using Linked Individual-based and Hydrodynamic Models to Interpret Patterns and Processes in the Oceanic Phase of Atlantic Menhaden *Brevoortia tyrannus* Life History (1999) *Fisheries Oceanography*, 8:suppl. 2:224-246.
Rabalais et al., Excess Nutrients from the Mississippi River Degrade Water Quality in the Gulf of Mexico (1998) *III. Agric. Pesticides Conference* pp. 94-102.
Rabalais et al., Nutrient Changes in the Mississippi River and System Responses on the Adjacent Continental Shelf (1996) *Estuaries* 19:386-407.
Rabalais, et al., Hypoxia in the Gulf of Mexico (2001) *J. of Environ. Qual.*, 30:320-329.

(56) References Cited

OTHER PUBLICATIONS

Rahman et al., Growth and Nutritional Trials on Transgenic Nile Tilapia Containing an Exogenous Fish Growth Hormone Gene (2001) *J. of Fish Biology* 59:62-78.

Raskoff et al., Collection and Culture Techniques for Gelatinous Zooplankton (2003) *Biol. Bull.* 204:68-80.

Raven, Nutritional and Neuroendocrine Control of Appetite in Transgenic Coho Salmon (Apr. 2006) Master of Science in Zoology, University of British Columbia [online], retrieved on Feb. 14, 2010 from the Internet site: https://circle.ubc.ca/bltstream/handle/2429/17748/ubc, pp. 2006-0292.pdf.

Raynie et al., A Comparison of Larval and Postlarval Gulf Menhaden, *Brevoortia patronus*, Growth Rates Between an Offshore Spawning Ground and an Estuarine Nursery (1994) *Fishery Bulletin* 92:890-894.

Redfield, The Biological Control of Chemical Factors in the Environment (1958) *American Scientist* 46:205-222.

Refstie, Long-term protein and lipid growth of Atlantic salmon (*Salmo salar*) fed diets with partial replacement of fish meal by soy protein products at medium or high lipid level (2001) *Aquaculture* 193:91-106.

Richardson, Remote Sensing of Algal Bloom Dynamics (1996) *BioScience* 46:492-501.

Rocha et al., Application of Inducible and Targeted Gene Strategies to Produce Transgenic Fish: A Review (2004) *Marine Biotechnology* 6:118-127.

Roelke, et al., The Diversity of Harmful Algal Bloom-Triggering Mechanisms and the Complexity of Bloom Initiation (2001) *Human and Ecological Risk Assessment* 7:1347-1362.

Roessler, Effects of Silicon Deficiency on Lipid Composition and Metabolism in the Diatom Cyclotella Cryptica (1988) *J. Phycol.* 24:394-400.

Selman et al., Eutrophication and Hypoxia in Coastal Areas: A Global Assessment of the State of Knowledge (2008) *WRI Policy Note* pp. 1-6.

Sheridan, Lipid Dynamics in Fish: Aspects of Absorption, Transportation, Deposition and Mobilization (1988) *Comp. Biochem. Physiol.* 90B:679-690.

Smith et al., Comparison of Biosequences (1981) *Adv. AppL Math.* 2:482-489.

Song et al., Creation of a Genetic Model of Obesity in Teleost (2007) *The FASEB Journal* 21:2042-2049.

Sournia et al., Marine Phytoplankton: How Many Species in the World Ocean? (1991) *J Plankton Res* 13:1093-1099.

Stuart et al., Filtration of Green Algae and Cyanobacteria by Freshwater Mussels in the Partitioned Aquaculture System (2001) *J. World Aquaculture Soc.* 32:105-111.

Symonds et al., Electroporation of Salmon Sperm with Plasmid DNA: Evidence of Enhanced Sperm/DNA Association (1994) *Aquaculture* 119:313-327.

Szelei et al., Liposome-Mediated Gene Transfer in Fish Embryos (1994) *Transgeneic Res.* 3:116-119.

Tave, Inbreeding and Brood Stock Management, *FAO Fisheries Technical Paper 392* (1999).

Tave, Selective Breeding Programmes for Medium-sized Fish Farms, *FAO Fisheries Technical Paper 352* (1995).

Taylor et al., Hybridization of *Cyprinus carpio* and *Carassius auratus*, the First Two Exotic Species in the Lower Laurentian Great Lakes (1977) *Environmental Biology of Fishes* 1:205-208.

Turker et al., Comparative Nile Tilapia and Silver Carp Filtration Rates of Partitioned Aquaculture System Phytoplankton (2003) *Aquaculture* 220:449-457.

Turker et al., Effect of Nile tilapia, *Oreochromis niloticus* (L.), Size on Phytoplankton Filtration Rate (2003) *Aquaculture Research* 34:1087-1091.

Turker et al., Effect of Temperature and Phytoplankton Concentration on Nile Tilapia *Oreochromis niloticus* (L.) Filtration Rate (2003) *Aquaculture Research* 34:453-459.

Turker et al., Filtration of Green Algae and Cyanobacteria by Nile Tilapia, *Oreochromis niloticus*, in the Partitioned Aquaculture System (2003) *Aquaculture* 215:93-101.

Turner et al., Fluctuating Silicate:Nitrate Ratios and Coastal Plankton Food Webs (1998) *Proc. Natl. Acad. Sci. USA* 95:13048-13051.

Turner, Element Ratios and Aquatic Food Webs (2002) *Estuaries* 25:694-703.

Vaughan et al., Assessment and Management of Atlantic and Gulf Menhaden Stocks (1991) *Marine Fisheries Review* 53:49-57.

Vaughan et al., Population Characteristics of Gulf Menhaden, *Brevoortia patronus* (2000) *NOAA Technical Report NMFS* 149:1-19.

Vega, Ocean Thermal Energy Conversion Primer (winter 2002/2003) *Mar Technol Soc J* 6:25-35.

Vijverberg, Culture techniques for studies on the growth, development and reproduction of copepods and cladocerans under laboratory and in situ conditions: a review (1989) *Freshwater Biology* 21:317-373.

Volkoff et al., Neuropeptides and the control of food intake in fish (2005) *General and Comparative Endocrinology* 142:3-19.

Wilkerson, Capturing the Potential in Waste Heat (1978) *Tennessee Valley Perspective* 9:4-10.

Zbikowska, Fish can be first—advances in fish transgenesis for commercial applications (2003) *Transgenic Research* 12:379-389.

Zelenin et al., The Delivery of Foreign Genes into Fertilized Fish Eggs Using High-Velocity Microprojectiles (1991) *FEES Letts.* 287:118-120.

Zohar et al., Endocrine Manipulations of Spawning in Cultured Fish: from Hormones to Genes (2001) *Aquaculture* 197:99-136.

\* cited by examiner

Figure 1: Schematic of Water Flow and Trophic Level Association in Molluscan Bivalve enhanced Microalgae Production Systems for Feeding Planktivorous Fish: Applications
1. Bioremediation of Eutrophic Zones in Marine and Freshwater Environments
2. Carbon Recycling and Carbon Capture in Marine and Freshwater Environments
3. Production of Fish and by products - Fish Meal, Fish Lipids and Biofuels in Marine and Freshwater Environments,

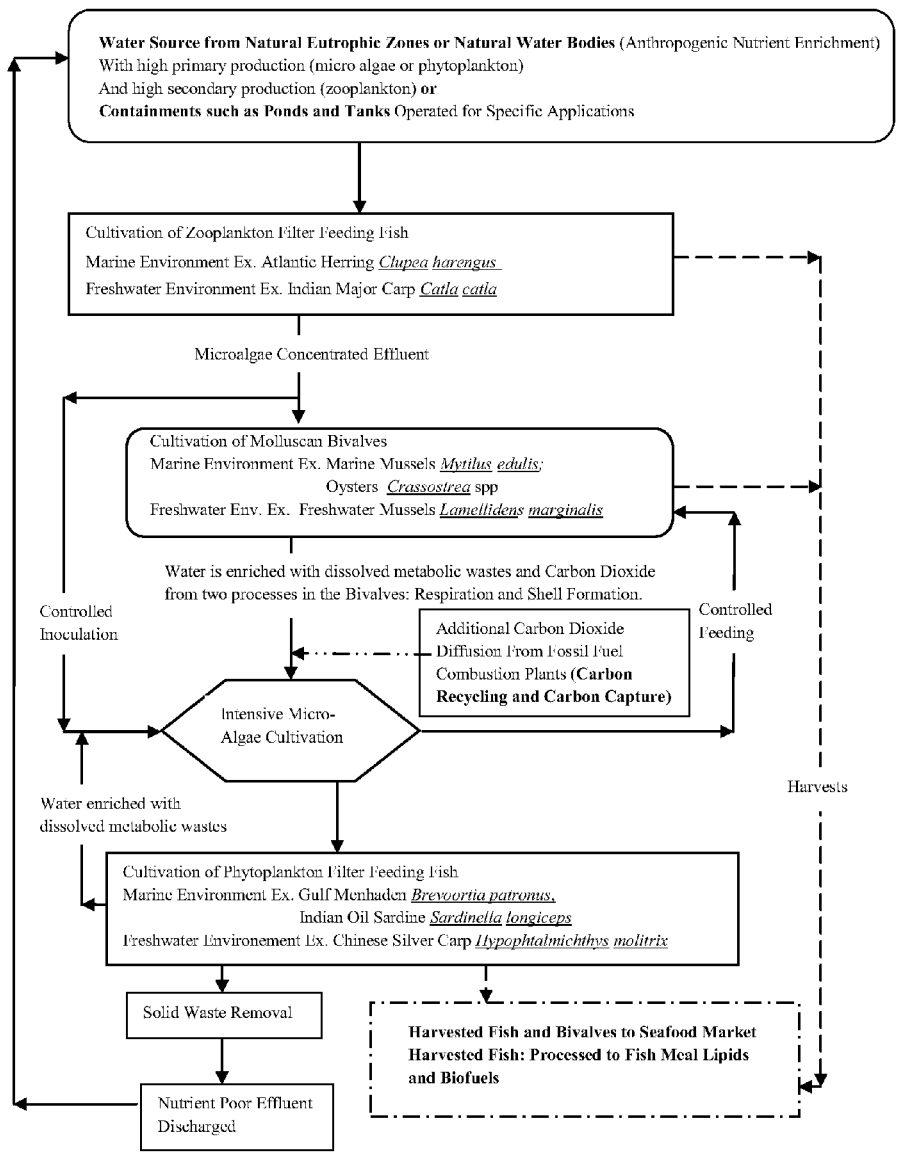

SYSTEMS AND METHODS FOR CULTURING ALGAE WITH BIVALVES

This application claims the benefit of U.S. Provisional Application No. 61/170,524, filed Apr. 17, 2009, which is incorporated by reference in its entirety.

1. INTRODUCTION

Provided herein are systems and methods for extracting lipids and/or producing biofuels from algae in marine and freshwater environments.

2. BACKGROUND OF THE INVENTION

The United States presently consumes about 42 billion gallons per year of diesel for transportation. In 2007, a nascent biodiesel industry produced 250 million gallons of a bio-derived diesel substitute produced from mostly soybean oil in the U.S. Biodiesel are fatty acid methyl esters (FAME) made typically by the base-catalyzed transesterification of triglycerides, such as vegetable oil and animal fats. Although similar to petroleum diesel in many physicochemical properties, biodiesel is chemically different and can be used alone (B100) or may be blended with petrodiesel at various concentrations in most modern diesel engines. However, a practical and affordable feedstock for use in biodiesel has yet to be developed that would allow significant displacement of petrodiesel. For example, the price of soybean oil has risen significantly in response to the added demand from the biodiesel industry, thus limiting the growth of the biodiesel industry to less than 1% of the diesel demand.

It has been proposed to use algae as a feedstock for producing biofuel, such as biodiesel. Some algae strains can produce up to 50% of their dried body weight in triglyceride oils. Algae do not need arable land, and can be grown with impaired water, neither of which competes with terrestrial food crops. Moreover, the oil production per acre can be nearly 40 times that of a terrestrial crop, such as soybeans. Although the development of algae presents a feasible option for biofuel production, there is a need to reduce the cost of producing the biofuel from algae. The fall in oil price in late 2008 places an even greater pressure on the fledgling biofuel industry to develop inexpensive and efficient processes. Provided herein is a cost-efficient approach for growing algae in a large scale for production of biofuel.

3. SUMMARY OF THE INVENTION

Provided herein are methods and systems for extracting lipids and/or producing biofuel from algae in marine and freshwater environments. In one embodiment, provided herein are methods for culturing algae comprising providing a source of water and a system comprising enclosures for culturing algae and culturing bivalves; culturing algae and bivalves in the system, whereby the level of at least one dissolved inorganic or organic nutrient in the water in the system is increased relative to water from the source; and feeding the algae to the bivalves at a rate such that the amount of algae produced in the system is greater than when the algae is cultured in the system without the bivalves. The dissolved nutrient can be carbon dioxide, ammonia, ammonium ion, a nitrite, nitrite ion, a nitrate, nitrate ion, a phosphate, orthophosphate ion, minerals, proteins, carbohydrates, or lipids. Also provided herein are methods for producing biofuel further comprising harvesting the algae by feeding the algae to the planktivorous fishes; extracting lipids from the planktivorous fishes; and polishing the lipids to form biofuel. Also provided herein are methods for extracting lipids from planktivorous fishes for other uses, such as for human consumption.

In certain embodiments, the bivalves are cultured in a bivalves enclosure separately from the algae cultured in a growth enclosure. Water in the bivalves enclosure that has an increased level dissolved nutrient(s) relative to the water from the source is flowed into the growth enclosure to sustain algae growth. Water from the growth enclosure and/or the fish enclosure are recirculated to the bivalves enclosure. In one embodiment, the effluent from the fish enclosure is flowed to the bivalves enclosure at a rate that allows the bivalves to feed on plankton that are not consumed by the plantivorous fishes. The residual plankton are generally of a size class that are not effectively retained or consumed by the planktivorous fish, e.g., less than 20 µm, about 10-20 µm, less than 10 µm, about 2-10 µm, less than 2 µm, and between 0.2-2 µm.

In another embodiment, the bivalves provided herein are used to condition water obtained from a source prior to using the water to culture the algae in the system. The methods comprise flowing water from a source into the bivalves enclosure, prior to flowing into the growth enclosure, such that the level of dissolved inorganic nutrient(s) is increased relative to the water from the source. The methods can further comprise removing zooplankton in water from the source, prior to flowing the water from the source into the bivalves enclosure. The removal of zooplankton can be accomplished by filtration or by allowing the water to flow through an enclosure comprising zooplankton-feeding organisms, at a rate that allows the organisms to feed on the zooplankton present in the water from the source. Zooplanktivorous fish, such as but not limited to, *Clupea harengus* (Atlantic herring, seawater) and *Catla catla* (Indian major carp, freshwater) can be used.

The systems provided herein generally comprise a source of water; a growth enclosure for culturing algae and a bivalves enclosure for culturing bivalves, wherein the growth enclosure and the bivalves enclosure are in fluid communication; means to regulate the rate, direction, or both the rate and direction, of fluid flow between the growth enclosure and the bivalves enclosure. Each of the enclosures can have a plurality of inlets and outlets to allow passage of fluids and matters, including algae and/or fishes, between the enclosures and other facilities of the system. The system also comprise means for culturing the bivalves and the algae; and means for feeding a controlled amount of the algae to the bivalves such that the amount of algae consumed by the bivalves do not result in a net loss of algae in the system over a period of time. The feeding of the bivalves can be controlled by adjusting the flow rate of an effluent from the growth enclosure to the bivalves enclosure and monitoring the concentration of the algae in the effluent. The systems can further comprise means for harvesting the algae by the planktivorous fishes; means for gathering the planktivorous fishes from which lipids are extracted and converted to biofuel; means for extracting lipids from the planktivorous fishes; and means for polishing the lipids to form biofuel.

4. BRIEF DESCRIPTION OF THE DRAWINGS

FIG. 1 shows an exemplary schematic of water flow and trophic level associations in the bivalves-enhanced algae culture system provided herein, which includes bivalves that supply carbon dioxide, and dissolved inorganic and organic nutrients, and filter plankton of a size smaller than those grazed by planktivorous fishes.

5. DETAILED DESCRIPTION OF THE INVENTION

Figure 2:
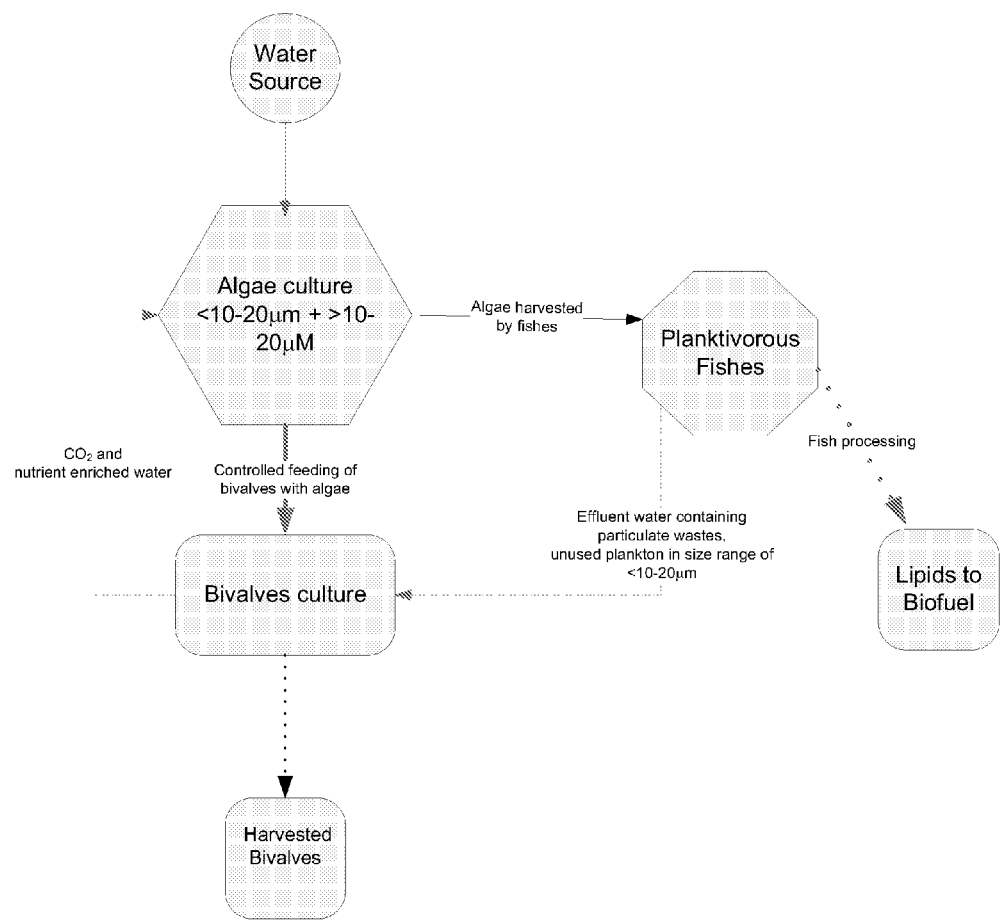
FIG. 2 shows another exemplary schematic of a systems provided herein, wherein algae less than 10 to 20 micrometers are not efficiently consumed by the planktivous fishes and are flowed into the bivalves enclosure for removal by the bivalves.

Provided herein are systems and methods for growing algae for extracting lipids and/or production of biofuel. The methods provided herein comprise growing algae in a system that comprises bivalves. The algae, fishes, and bivalves are cultured under conditions that promote nutrient recycling, resulting in gains in algal biomass as well as fish and bivalves biomass. Unlike aquaculture operations where algae is grown as feed for marine invertebrate larvae, the algae provided herein are cultured to accumulate lipids for use as energy feedstocks. The algae are harvested by fish, and the lipids extracted from fish are used to make biofuel. The bivalves cultured in the operation can optionally be sold, as animal feed or human food depending on the species and the market. Depending on the location of the system, the methods provided herein can also be used to remediate eutrophic zones, and enable carbon capture.

Using algae to produce energy feedstock at an industrial scale requires a cost-effective and sustainable supply of nutrients. The scale of algae culture required dwarfs those of existing culture systems that are designed to produce nutritional supplement, fine chemicals, or aquaculture feed. The costs of carbon, nitrogen and phosphorous must be carefully managed, and any savings and recycling of these nutrients can be significant for a culture system at this scale. The culture system must also be efficient in yielding algal biomass, and remain stable despite seasonal and other environmental changes. The bivalves in the algae culture systems provide various benefits in these respects, and generally promote the efficient turnover of nutrients within the system. Without being bound by any theory, the bivalves that are cultured in the system serve as a supplementary source of carbon dioxide, nitrogen and/or phosphorous.

Carbon nutrition is a significant component in the operating cost of a commercial algal culture facility. Photosynthetic algae take up dissolved $CO_2$ (inorganic carbon) and inorganic nutrients, and produce organic carbon in the form of algal biomass. For high rates of autotrophic production, atmospheric $CO_2$ alone cannot satisfy the requirement. The diffusion rate of $CO_2$ from atmosphere into open ponds have been estimated to sustain productivities at about 10 g dry weight per m² per day. In one embodiment, bivalves contribute carbon dioxide to the system, which carbon dioxide is produced as a result of respiration and formation of bivalves shells.

In surface seawater with a pH of about 8.1, about 90% of the inorganic carbon is bicarbonate ion, 9% is carbonate ion, and only 1% is dissolved $CO_2$. The equilibrium is governed by a series of reactions:

$$CO_2 \text{ atm} \leftrightarrow CO_2 \text{ aq} + H_2O \leftrightarrow H_2CO_3 \leftrightarrow H^+ + HCO_3^- \leftrightarrow 2H^+ + CO_3^{2-}$$

The bicarbonate-carbonate buffer system is important in freshwater and marine cultures for controlling pH and can be used to provide $CO_2$ for photosynthesis. When $CO_2$ is dissolved in water, it forms weak carbonic acid which then dissociate by losing hydrogen ions to form bicarbonate ($HCO_3^-$) and carbonate ($CO_3^{2-}$) ions. Uptake of $CO_2$ for photosynthesis and its release by respiration are major processes by which organisms alter the concentration of $CO_2$.

The bicarbonate-carbonate buffer system in water can provide $CO_2$ for photosynthesis through the following reactions:

$$2HCO_3^- \leftrightarrow HCO_3^{2-} + H_2O + CO_2$$

$$HCO_3^- \leftrightarrow OH^- + CO_2$$

$$CO_3^{2-} + H_2O \leftrightarrow CO_2 + 2OH^-$$

As a result of $CO_2$ fixation, hydroxyl groups are produced which lead to a gradual increase in pH in the water. Sparging $CO_2$ directly into the algal culture is commonly used to control pH and provide carbon nutrition. However, for shallow suspensions at near neutral pH, the residence time of the $CO_2$ bubbles are insufficient for dissolution, resulting in continuous loss to the atmosphere. Certain methods provided herein can reduce the operating cost of an algae facility by providing a supplementary source of $CO_2$ for the algal culture. The bivalves are particularly beneficial when carbon dioxide is a limiting factor at times in primary production, such as, in eutrophic water where nitrogen and phosphorous is not limiting.

Precipitation and dissolution of calcium carbonate in the shells and structural components of bivalves plays a role in the cycling of inorganic carbon. When calcium carbonate is precipitated, $CO_2$ is generated rather than consumed. Calcification induces shifts in the seawater carbonate equilibrium to generate dissolved $CO_2$ from inorganic carbon. The deposition of one mole of calcium carbonate ($Ca^{2+} + 2 HCO_3^- \rightarrow CaCO_3 + H_2O + CO_2$) releases nearly one mole of $CO_2$ in freshwater and 0.6 mole $CO_2$ in seawater (Ware et al., 1991, Coral Reefs 11:1270-120). The water becomes more acidic due to the removal of bicarbonate and carbonate ions. The increase in partial pressure of $CO_2$ from biogenic calcification has been studied (Berger et al., 1982, Naturwissenschaften 69:87-88), and it has been confirmed that calcification and respiration of invasive bivalves is a biogenic source of $CO_2$ (Chauvaud et al., 2003, Limnol. Oceangr. 48:2086-2092).

Calcium is a necessary component for shell secretion and formation. Many organisms do not survive when the level of calcium in the water column falls below a threshold which is about 5 mg/l. Depending in part on the species being used, the minimum concentration of calcium required ranges from about 25 to 150 mg/l. Calcifying organisms, such as bivalves, exert a variable degree of control over the process of calcification. Growth of the shell of bivalves is governed by the synthesis of an organic matrix and $CaCO_3$ crystal growth on the matrix. The amount of calcium in the shell is a function of the calcium level in ambient water, the amount of water pumped across the animal's tissues, the local pH and buffering capacity, the metabolism of the animal, and temperature that controls the rate of the physiologic processes.

Nitrogen is an element that is after carbon the most important and often limiting element to aquatic organisms. Compared to carbon that has one inorganic form, nitrogen exists in several forms in the environment, i.e., ammonium, nitrite, nitrate, dissolved nitrogen gas. Nitrogen also exists as dissolved organic nitrogen and particulate organic nitrogen in the system. Input of nitrogen from fixation of atmospheric nitrogen by bacteria is not sufficient to support the needs of a growing algal culture. Phosphorous is essential for the metabolic process of energy transfer in both photosynthesis and respiration. In aquatic environments, phosphorous is found in the water column as dissolved inorganic phosphorous (usually orthophosphate), as dissolved organic phosphorous, and as particulate organic phosphorous. Phosphate release from sediments is affected by adsorption-desorption equilibrium of phosphate with iron hydroxides. When the sediments are anoxic, the strongly reducing environment is conducive to release of phosphate into water. Traditional fishery practices address the shortfall by adding fertilizers and/or manure to the water.

Bivalves filter water continuously at a high rate (up to 8 gallons per hour), and can thus recycle nutrients that are limiting in the system, thereby increasing primary production. Bivalves process nutrient materials by consuming pelagic or suspended particulate organic matters, and excreting dissolved organic and inorganic matters. Particulate organic matters include phytoplankton, zooplankton, bacteria, and detritus. Suspended organic detritus often has bacteria attached, and these bacteria are decomposing as well as assimilating the carbon in the detritus. Dissolved inorganic matters include but is not limited to ammonia and orthophosphates. Dissolved organic matters, include but is not limited to amino acids, proteins, carbohydrates, and lipids. In one embodiment, dissolved organic and inorganic materials produced by bivalves provided herein and released in the water of the system are readily taken up by the algae for growth. Exemplary species of bivalves include but are not limited to *Mytilus edulis* (marine mussels), *Crassostrea* species (oysters), *Lamellidens marginalis* (freshwater mussels).

A number of feeding mechanisms have evolved in bivalves. Filter-feeding bivalves pump large volume of water and filter this water to remove suspended particulate materials. A variety of particles of different qualitative nutrient values in the water are pumped through the bivalve gills acting as filters. Usually water enters the mantle cavity through the inhalant siphon, moves over the gills, and leaves through the exhalent siphon. Particles that are too large are rejected as pseudofeces and particles that are too small pass through the gills. The rejected particles are wrapped in mucus, and are expelled without having passed through the digestive tract. The pseudofeces sink and become available as nutrients for use by benthic organisms and bacteria. Bivalves, and pseudofeces-producing bivalves in particular, are very efficient in the transfer of suspended particulate matters from the pelagic environment to the benthic environment. Deposit-feeding bivalves generally inhabit muddy benthic environment, remove deposited sediments from the benthic environment to extract organic matter, and release inorganic wastes. In coastal water, a sizeable proportion of nutrients for primary production is provided by mineralization of particulate matter by benthic organisms. Depending on the environment, filter-feeding bivalves and/or deposit-feeding bivalves can be used in the systems provided herein. Feces and pseudofeces, produced by the bivalves falls to and enrich the sediments surrounding the bivalves where benthic organisms, mostly bacteria, decompose the organic matters and release inorganic nutrients which can be used by the algae in the system. Metabolic activities of the benthic organisms consume oxygen and sustain a hypoxic, reducing environment in the sediment which favors the release of soluble inorganic phosphate from Fe(III)-bound phosphate complexes. The released dissolved phosphate can be used by the algae of the system.

In certain embodiments, the algae produced in the culture system are harvested by planktivorous fishes, such as but not limited to *Brevoortia patronus* (Gulf menhaden), *Sardinella longiceps* (Indian oil sardine), and *Hypophalmichthys molitrix* (Chinese silver carp). As prey size is a major factor affecting planktivore predation, the age or ontogenetic form of the fishes are selected such that the eyesight, locomotion, mouth dimensions, dentition, and gut dimension permit the fishes to ingest efficiently the dominant species of algae cultured in the system. However, there are smaller plankton in the water that pass through the gills of the selected plantivorous fishes, and thus remain in the water. The plankton in this size class includes phytoplankton, zooplankton and bacteria. A growing abundance of such smaller residual plankton, if left unchecked in the water of the system, can compete with other algae for nutrients and light, and can also encourage the expansion of a zooplankton population in the system. The occurrence of such events can make the system less efficient, destabilize the system by changing the trophic structure, and lead to a collapse of the algae culture. The removal of plankton in this size class from the water by the bivalves can prevent accumulation or overgrowth of such plankton, and thus maintain stability of the systems provided herein. In another embodiment, the bivalves stabilize the systems provided herein by filtering plankton that are too small to be harvested efficiently by the fishes in the system.

Algae inhabit all types of aquatic environment, including but not limited to freshwater, marine, and brackish environment. Accordingly, in certain embodiments, provided herein are selected species of algae and bivalves in any of such aquatic environments. The algal culture can comprise a population of algae of one or more species, and the population of bivalves can comprise a single species of bivalves or multiple species. The term "algal composition" refers to any composition that comprises algae and is not limited to the culture in which the algae are cultivated. It is contemplated that an algal composition can be prepared by mixing different algae from a plurality of algal cultures. As used herein, the term "growth enclosure" refers to a water enclosure in which the algae are grown. The majority of algal growth takes place in the growth enclosure which is designed and equipped to optimize algal growth. In addition, the systems provided herein can comprise, independently and optionally, enclosures for culturing fishes that harvest the algae, enclosures for culturing bivalves, enclosures for preparing a starter algal culture, enclosures in which zooplankton is removed, bivalves husbandry units, and biomass storage units. The bivalves husbandry units provide the environments in which the bivalves are stocked, bred, incubated, or maintained.

The algae and the bivalves that are used in the methods provided herein are described in Section 5.1 and 5.2 respectively. As used herein the term "system" refers to the installations for practicing the methods provided herein. The methods and systems provided herein for culturing algae are described in Section 5.3. Technical and scientific terms used herein have the meanings commonly understood by one of ordinary skill in the art, unless otherwise defined. Reference is made herein to various methodologies known to those of skill in the art. Publications and other materials setting forth such known methodologies to which reference is made are incorporated herein by reference in their entireties as though set forth in full. The practice of the methods and systems provided herein will employ, unless otherwise indicated, techniques of chemistry, biology, and the aquaculture industry, which are within the skill of the art. Such techniques are explained fully in the literature, e.g., Estuarine and Marine Bivalve Mollusk Culture, Menzel B. 1991, CRC press, Boca Raton, Fla., USA; Handbook of Microalgal Culture, edited by Amos Richmond, 2004, Blackwell Science; Limnology: Lake and River Ecosystems, Robert G. Wetzel, 2001, Academic Press, each of which are incorporated by reference in their entireties.

As used herein, "a" or "an" means at least one, unless clearly indicated otherwise. The term "about," as used herein, unless otherwise indicated, refers to a value that is no more than 20% above or below the value being modified by the term. For clarity of disclosure, and not by way of limitation, the detailed description is divided into the subsections which follow.

5.1. Algae

As used herein the term "algae" refers to any organisms with chlorophyll and a thallus not differentiated into roots, stems and leaves, and encompasses prokaryotic and eukaryotic organisms that are photoautotrophic or photoauxotrophic. The terms "microalgae" and "phytoplankton," used interchangeably herein, refer to any microscopic algae, photoautotrophic or photoauxotrophic protozoa, and cyanobacteria (formerly classified as Cyanophyceae). The use of the term "algal" also relates to microalgae and thus encompasses the meaning of "microalgal." These microscopic aquatic organisms are also encompassed by the term "plankton." While the term plankton includes both phytoplankton and zooplankton, it is contemplated that certain embodiments provided herein can be practiced without isolation of the phytoplankton or removal of the zooplankton. The culturing and harvesting methods provided herein are applicable to a body of water comprising plankton and fishes.

The algae that are cultured or harvested by the methods provided herein are grown using solar power as its energy source, although algae can also be grown under artificial light and be similarly harvested. The algae provided herein can be a naturally occurring species. The algae can be a transgenic strain, a genetically manipulated strain, or a selected strain, that bears certain beneficial traits, such as but not limited to, increased growth rate, lipid accumulation, favorable lipid composition, adaptation to certain environment, and robustness in changing environmental conditions. In some embodiments, it is desirable that the algae accumulate excess lipids and/or hydrocarbons. In other embodiments, this is not a requirement since algal cells with relatively lower lipids level but higher carbohydrate level can also be useful, because the carbohydrates can be converted to lipids metabolically by the harvesting fish.

Algae, including microalgae, inhabit all types of aquatic environment, including but not limited to freshwater (less than about 0.5 parts per thousand (ppt) salts), brackish (about 0.5 to about 31 ppt salts), marine (about 31 to about 38 ppt salts), and briny (greater than about 38 ppt salts) environment. As certain embodiments provided herein can be practiced in any of such aquatic environments, freshwater species, marine species, and/or species that thrive in varying and/or intermediate salinities or nutrient levels, can be used. The algae used in the algal culture can be obtained initially from environmental samples of natural or man-made environments, and may contain a mixture of prokaryotic and eukaryotic organisms, wherein some of the minor species may be unidentified. Freshwater filtrates from rivers, lakes; seawater filtrates from coastal areas, oceans; water in hot springs or thermal vents; and lake, marine, or estuarine sediments, can be used to source the algae. The samples may also be collected from local or remote bodies of water, including surface as well as subterranean water.

Endemic or indigenous species are generally preferred over introduced species where an open farming system is used. Endemic or indigenous species may be enriched or isolated from water samples obtained locally (relative to the site of the culture system). It can also be beneficial to deploy algae and fishes from a local aquatic trophic system in the harvesting methods provided herein. Depending on the location of the algae culture system, algae obtained from tropical, subtropical, temperate, polar or other climatic regions can be used.

According to certain embodiments provided herein, one or more species of algae will be present in the algal culture, or the algal composition that is to be harvested by fish. In one embodiment, the algal culture is a monoculture, wherein only one species of algae is grown. However, in many open systems, it may be difficult to avoid the presence of other algae in the water. Accordingly, a monoculture may comprise about 0.1% to 2% of algae species other than the intended species. In another embodiments, the algal culture is a mixed culture that comprises one or several species of algae, i.e., the algal culture is not a monoculture. In certain embodiments, especially when an open system is in use, the composition of algae in the algal culture can change seasonally; the body of water can comprise zooplankton. The algae in an algal culture provided herein may not all be cultivable under laboratory conditions. Not all the algae in an algal culture provided herein have to be taxonomically classified or characterized in order to be utilized in certain embodiments provided herein. Algal cultures and algal compositions can generally be distinguished by the relative proportions of the major groups of algae that are present.

Chlorophyll a is a commonly used indicator of algal biomass. However, it is subjected to variability of cellular chlorophyll content (0.1 to 9.7% of fresh algal weight) depending on algal species. An estimated biomass value can be calibrated based on the chlorophyll content of the dominant species within a population. Published correlation of chlorophyll a concentration and biomass value can be used in certain embodiments provided herein. Generally, chlorophyll a concentration is to be measured within the euphotic zone of a body of water. The euphotic zone is the depth at which the light intensity of the photosynthetically active spectrum (400-700 nm) equals 1% of the subsurface light intensity.

A mixed algal culture provided herein comprises one or several dominant species of macroalgae and/or microalgae. Microalgal species can be identified by microscopy and enumerated by counting or flow cytometry, which are techniques well known in the art. A dominant species is one that ranks high in the number of algal cells, e.g., the top one to five species with the highest number of cells relative to other species. The one or several dominant algae species may constitute greater than about 10%, about 20%, about 30%, about 40%, about 50%, about 60%, about 70%, about 80%, about 90%, about 95%, about 97%, about 98% of the algae present in the culture. In certain embodiments, several dominant algae species may each independently constitute greater than about 10%, about 20%, about 30%, about 40%, about 50%, about 60%, about 70%, about 80% or about 90% of the algae present in the culture. Many other minor species of algae may also be present in such culture but they may constitute in aggregate less than about 50%, about 40%, about 30%, about 20%, about 10%, or about 5% of the algae present. In various embodiments, one, two, three, four, or five dominant species of algae are present in a culture. Accordingly, a mixed algal culture or an algae composition can be described and distinguished from other cultures or compositions by the dominant species of algae present. The composition and culture can be further described by the percentages of cells that are of dominant species relative to minor species, or the percentages of each of the dominant species. The identification of dominant species can also be limited to species within a certain size class, e.g., from about 200 to 2000 µm, about 20 to 200 µm, about 2 to 20 µm, or below 2 µm. It is to be understood that mixed algal cultures or compositions having the same genus or species of algae may be different by virtue of the relative abundance of the various genus and/or species present.

It is contemplated that many different algal cultures or bodies of water which comprise plankton, can be cultured and/or harvested efficiently by the methods provided herein. Microalgae are preferably used in certain embodiments provided herein; while macroalgae can be less preferred in certain embodiments. In specific embodiments, algae of a particular taxonomic group, genera or species, may be less preferred. Such algae, including one or more that are listed below, may be specifically excluded as a dominant species in a culture. However, it should also be understood that in certain embodiments, such algae may be present as a contaminant especially in an open system, or as a non-dominant group or minor species. Such algae may be present in negligent numbers, or substantially diluted given the volume of the culture. The presence of such algal genus or species in a culture or a body of water comprising plankton is distinguishable from cultures or other bodies of water where such genus or species are dominant, or constitute the bulk of the algae.

In certain embodiments, an algal composition comprising a combination of different groups of algae can be used. The algal composition can be prepared by mixing a plurality of different algal cultures. The different groups of algae can be present in defined proportions. The combination and proportion of different algae in the algal composition can be designed to enhance the growth and/or accumulation of lipids of certain groups or species of fish.

In certain embodiments, one or more species of algae belonging to the following phyla can be cultured and/or harvested by the methods provided herein: *Cyanobacteria, Cyanophyta, Prochlorophyta, Rhodophyta, Glaucophyta, Chlorophyta, Dinophyta, Cryptophyta, Chrysophyta, Prymnesiophyta (Haptophyta), Bacillariophyta, Xanthophyta, Eustigmatophyta, Rhaphidophyta*, and *Phaeophyta*. In certain embodiments, algae in multicellular or filamentous forms, such as seaweeds or macroalgae, many of which belong to the phyla *Phaeophyta* or *Rhodophyta*, are less preferred. In many embodiments, algae that are microscopic, are preferred. Many such microalgae occurs in unicellular or colonial form.

In certain embodiments, the algal culture or the algal composition to be harvested by the methods provided herein comprises cyanobacteria (also known as blue-green algae) from one or more of the following taxonomic groups: Chroococcales, Nostocales, Oscillatoriales, Pseudanabaenales, Synechococcales, and Synechococcophycideae. Non-limiting examples include *Gleocapsa, Pseudoanabaena, Oscillatoria, Microcystis, Synechococcus* and *Arthrospira* species.

In certain embodiments, the algal culture or the algal composition to be harvested comprises algae from one or more of the following taxonomic classes: Euglenophyceae, Dinophyceae, and Ebriophyceae. Non-limiting examples include *Euglena* species and the freshwater or marine dinoflagellates.

In certain embodiments, the algal culture or the algal composition to be harvested comprises green algae from one or more of the following taxonomic classes: Micromonadophyceae, Charophyceae, Ulvophyceae and Chlorophyceae. Non-limiting examples include species of *Borodinella, Chlorella* (e.g., *C. ellipsoidea*), *Chlamydomonas, Dunaliella* (e.g., *D. salina, D. bardawil*), *Franceia, Haematococcus, Oocystis* (e.g., *O. parva, O. pustilla*), *Scenedesmus, Stichococcus, Ankistrodesmus* (e.g., *A. falcatus*), *Chlorococcum, Monoraphidium, Nannochloris* and *Botryococcus* (e.g., *B. braunii*). In certain embodiments, *Chlamydomonas reinhardtii* are less preferred.

In certain embodiments, the algal culture or the algal composition to be harvested comprises golden-brown algae from one or more of the following taxonomic classes: Chrysophyceae and Synurophyceae. Non-limiting examples include *Boekelovia* species (e.g. *B. hooglandii*) and *Ochromonas* species.

In certain embodiments, the algal culture or the algal composition to be harvested comprises freshwater, brackish, or marine diatoms from one or more of the following taxonomic classes: Bacillariophyceae, Coscinodiscophyceae, and Fragilariophyceae. Preferably, the diatoms are photoautotrophic or auxotrophic. Non-limiting examples include *Achnanthes* (e.g., *A. orientalis*), *Amphora* (e.g., *A. coffeiformis* strains, *A. delicatissima*), *Amphiprora* (e.g., *A. hyaline*), *Amphipleura, Chaetoceros* (e.g., *C. muelleri, C. gracilis*), *Caloneis, Camphylodiscus, Cyclotella* (e.g., *C. cryptica, C. meneghiniana*), *Cricosphaera, Cymbella, Diploneis, Entomoneis, Fragilaria, Hantschia, Gyrosigma, Melosira, Navicula* (e.g., *N. acceptata, N. biskanterae, N. pseudotenelloides, N. saprophila*), *Nitzschia* (e.g., *N. dissipata, N. communis, N. inconspicua, N. pusilla* strains, *N. microcephala, N. intermedia, N. hantzschiana, N. alexandrina, N. quadrangula*), *Phaeodactylum* (e.g., *P. tricornutum*), *Pleurosigma, Pleurochrysis* (e.g., *P. carterae, P. dentata*), *Selenastrum, Surirella* and *Thalassiosira* (e.g., *T. weissflogii*).

In certain embodiments, the algal culture or the algal composition to be harvested comprises planktons that are characteristically small with a diameter in the range of 1 to 10 rpm, or 2 to 4 μm. Many of such algae are members of *Eustigmatophyta*, such as but not limited to *Nannochloropsis* species (e.g. *N. salina*).

In certain embodiments, the algal culture or the algal composition to be harvested comprises one or more algae from the following groups: *Coelastrum, Chlorosarcina, Micractinium, Porphyridium, Nostoc, Closterium, Elakatothrix, Cyanosarcina, Trachelamonas, Kirchneriella, Carteria, Crytomonas, Chlamydamonas, Planktothrix, Anabaena, Hymenomonas, Isochrysis, Pavlova, Monodus, Monallanthus, Platymonas, Pyramimonas, Stephanodiscus, Chroococcus, Staurastrum, Netrium*, and *Tetraselmis*.

In certain embodiments, any of the above-mentioned genus and species of algae may independently be less preferred as a dominant species in, or excluded from, an algal composition provided herein.

5.2 Bivalves

As used herein, the term bivalves refers to any exoskeleton-bearing invertebrate animals of the class Bivalvia in phylum Mollusca. The term is not limited to species that are consumed by humans as food. When referring to a plurality of organisms, the term "bivalve" is used interchangeably with the term "bivalves" regardless of whether one or more than one species are present, unless clearly indicated otherwise. In certain embodiments, bivalves useful for the methods and systems provided herein can be obtained from hatcheries or collected from the wild. The bivalves may be spats, larvae, trochophores, veligers, pediveligers, juveniles, or mature bivalves. The bivalves may reproduce in an enclosure within the system but not necessarily in the same enclosure as the algae culture. Any bivalves aquaculture techniques known in the art can be used to stock, maintain, reproduce, and harvest the bivalves useful for the methods and systems provided herein.

According to certain embodiments provided herein, the algae reside in the same body of water as a population of bivalves. In one embodiment, the bivalves population comprises only one species of bivalves. In another embodiment, the bivalves population is mixed and thus comprises one or several major species of bivalves. A major species is one that ranks high in the head count, e.g., the top one to five species with the highest head count relative to other species. The one or several major bivalves species may constitute greater than about 10%, about 20%, about 30%, about 40%, about 50%, about 60%, about 70%, about 75%, about 80%, about 90%, about 95%, about 97%, about 98% of the bivalves present in the population. In certain embodiments, several major bivalves species may each constitute greater than about 10%, about 20%, about 30%, about 40%, about 50%, about 60%, about 70%, or about 80% of the bivalves present in the population. In various embodiments, one, two, three, four, five major species of bivalves are present in a population. Accordingly, a mixed bivalves population or culture can be described and distinguished from other populations or cultures by the major species of bivalves present. The population or culture can be further described by the percentages of the major and minor species, or the percentages of each of the major species. It is to be understood that mixed cultures having the same genus or species may be different by virtue of the relative abundance of the various genus and/or species present.

Bivalves inhabits most types of aquatic environment, including but not limited to freshwater, marine, brackish, and briny environment. In certain embodiments, as the methods and systems provided herein can be practiced in any of such aquatic environments, any freshwater species, stenohaline species, euryhaline species, marine species, species that grow in brine, and/or species that thrive in varying and/or intermediate salinities, can be used. Bivalves from tropical, subtropical, temperate, polar, and/or other climatic regions can be used. Bivalves that live within the following temperature ranges can be used: below 10° C., 9° C. to 18° C., 15° C. to 25° C., 20° C. to 32° C. In one embodiment, bivalves indigenous to the region at which the methods provided herein are practiced, are used. Preferably, bivalves from the same climatic region, same salinity environment, or same ecosystem, as the algae are used.

Bivalves use several mechanisms for feeding. Some species can use more than one mechanism to feed, depending on the conditions of the environment. In one embodiment, the population of bivalves comprises exclusively or predominantly filter feeding species. In another embodiment, the population of bivalves comprises exclusively or predominantly deposit feeding species. In yet another embodiment, the population of bivalves comprises exclusively or predominantly species that contains photoautotrophic symbionts (zooxanthellae) and/or chemotrophic symbionts. The chemotrophic symbionts are mostly bacteria that reside in extracellular or intracellular locations. The chemotrophic symbionts include lithotrophic and methanotrophic organisms. In a preferred embodiment, the major species of bivalves in the population are not phytoplanktivores that would consume significant amounts of the growing algae. In certain mixed bivalves population provided herein, filter feeding and deposit feeding species are both present. In addition to filter feeding and deposit feeding species, species that contain photoautotrophic and/or chemoautotrophic symbionts are also present in a mixed bivalves population provided herein.

Bivalves from different taxonomic groups can be used in the enclosure. It should be understood that, in various embodiments, bivalves within a taxonomic group, such as a family or a genus, can be used interchangeably in various methods provided herein. Certain embodiments provided herein are described below using common names of bivalves groups and bivalves, as well as the scientific names of exemplary species. Databases, such as the Ocean Biogeographic Information System by World Wide Web electronic publication, www.iobis.org, version (03/2009), provide additional useful bivalves species within each of the taxonomic groups that are useful in certain embodiments provided herein. It is contemplated that one of ordinary skill in art could, consistent with the scope of certain embodiments provided herein, use the databases to specify other species within each of the described taxonomic groups for use in the methods provided herein.

The selection of bivalves for use in the methods provided herein depends on a number of factors. Some of the most important factors are the compatibility of the cultured algae and the bivalves. Preferably, the algae culture grows well using the carbon dioxide and metabolic waste produced by the selected bivalves, thereby reducing the need to add $CO_2$ and to fertilize the water. Preferably, the population of bivalves is self-sustaining and does not require extensive husbandry efforts to promote reproduction and rear the larvae. The methods provided herein can employ species of bivalves that are used as human food, to offset the cost of operating the algae culture.

A representative group of bivalves that are useful in certain embodiments provided herein is the mollusks. Mollusks in the classes, Bivalvia and Gastropoda, are of particular interest. Within the class of bivalves are several orders which include many ecologically and commercially important species, such as but not limited to, Mytiloida (Mytilidae (sea mussels)); Ostreoida (Pectimidae, Ostreidae, Unionoida (freshwater mussels); Myoida, Pterioida (Pteriidae, pearl oysters), and Veneroida (Tridacnidae, Lucimidae). Within Gastropoda are subclasses of organisms that produce pearl, e.g., Patellogastropoda, Vetigastropoda, Littprinoida, Tonnida, Muricoida and Pulmonata.

The bivalves used in the methods provided herein are preferably sessile or sedentary and of commercial value, including but not limited to oysters, mussels, scallops, and clams. Exemplary species include but are not limited to, Crassostrea species such as *C. gigas, C. virginica, C. ariakensis, C. rivularis, C. angulata, C. eradelie, C. commercialis,* Saccostrea species such as *S. glomerata, S. cucculata* and *S. commercialis,* Mercenaria species such as *M. mercenaria* and *M. campechensis,* Ostrea species such as *O. edulis, O. chilensis,* and *O. lurida, Arca transversa, Panope generosa, Saxodomus nuttili,* Mytilus species such as *M. edulis* (blue mussel), *M. coruscus, M. chilensis, M. trossulus,* and *M. galloprovincialis* (Mediterranean mussel), *Aulacomya ater, Choromytilus chorus, Tapes semidecussatus,* Perna species such as *P. viridis, P. canaliculus,* Venerupis species such as *V. decussata, V. semidecussata, Sinonovacula constricta* (Razor clam), *Spisula solidissima* (surf clams), *Amusium balloti, Argopecten irradians* (bay scallops), Pectan species such as *P. alba, P. yessonsis, P. maximus,* Pinctada species such as *P. margaritifera, P. radiate, P. maxima, P. fucata, P. albina,* Hyriopsis species, such as *H. cumingii, H. schlegelii,* Tridacnidae species, such as *Tridacna gigas* (giant clam), Lamellidens species, such as *L. marginalis* (freshwater mussels), *L. corrianus,* and Chlamys species such as *C. farreri, C. opercularis, C. prpuratus* and *C. varia*.

Although native species are preferably used, non-native species that has already invaded a particular body of water can also be used, e.g., Dreissena species such as *D. polymorpha* (zebra mussels), *D. bugenesis* (quagga mussels) and *D. rostiformis,* Corbiucla species such as *C. fluminea* (Asian clam).

5.3 Methods and Systems

Provided herein are methods and systems for growing algae to extract lipids and/or produce biofuel. According to certain embodiments provided herein, the algae as described in Section 5.1 and the bivalves as described in Section 5.2 are cultured for a period of time in a circulating body of water in the systems. The algae are cultured in the same body of water as the bivalves in the system, wherein at least one dissolved inorganic or organic nutrients provided by the bivalves enable the algae to grow more efficiently than in the absence of the bivalves. For example, the algae culture may require less carbon dioxide, nitrogen fertilizer, and/or phosphorous fertilizer. The dissolved inorganic nutrient can be carbon dioxide, ammonia, ammonium ion, a nitrite, nitrite ion, a nitrate, nitrate ion, a phosphate, or orthophosphate ion. Organic nutrients include amino acids, proteins, lipids, and carbohydrates. However, it is not required that the bivalves and the algae be cultured together in the same enclosure or throughout the entire culturing process. In one embodiment, the bivalves and the algae reside in the same enclosure but the bivalves reside in a zone within the enclosure, such as the benthic layer. In other embodiments, the bivalves and algae are cultured separately. The systems provided herein can comprise a source of water, a plurality of enclosures and means for growing algae, bivalves, and/or fishes, particularly, a growth enclosure for culturing algae, a fish enclosure for culturing planktivorous fishes, and a bivalves enclosure for culturing bivalves. The growth enclosure, the fish enclosure, and the bivalves enclosure are each in fluid communication with the other enclosures, and means to regulate independently the rate, direction, or both the rate and direction, of fluid flow between each of the bivalves enclosure, the growth enclosure and the fish enclosure are also provided.

The bivalves, growth, and fish enclosures can be but not limited to raceways, rectangular tanks, circular tanks, partitioned tanks, plastic bags, earthen ponds, lined ponds, channels, and artificial streams. The enclosures of the systems provided herein are connected by channels, hoses, and pipes. The rate, direction, or both rate and direction of flow is controlled by pumps, valves, and gates. The bivalves enclosure may comprise embedded, submerged or floating substrates, such as ropes, racks, and tubes. Preferably, the bivalves enclosure comprises a sedimentary bottom and a benthic community of organisms, such that solid wastes produced by the bivalves can be remineralized by the benthic organisms and bacteria. The enclosures provided herein can be set up according to knowledge known in the art, see, for example, Chapters 13 and 14 in Aquaculture Engineering, Odd-Ivar Lekang, 2007, Blackwell Publishing Ltd., respectively, for description of closed production systems and open farming systems.

The mode of algal culture can be a batch culture, a continuous culture, or a semi-continuous culture. A batch culture comprises providing a single inoculation of algal cells in a volume of water in the growth enclosure followed by a growing period and finally harvesting the algal population when it reaches a desirable density. Typically, the growth of algae is characterized by a lag phase, a growth phase, and a stationary phase. The lag phase is attributed to physiological adaptation of the algal metabolism to growth. Cultures inoculated with exponentially growing algae have short lag phases and are thus desirable. Cell density increases as a function of time exponentially in the growth phase. The growth rate decreases as nutrient levels, carbon dioxide, unfavorable pH, or other environmental factors become limiting in a stationary phase culture. When a growing algae culture has outgrown the maximum carrying capacity of an enclosure, the culture can be transferred to one or several growth enclosures with a lower loading density. The initial algal culture is thereby diluted allowing the algae to grow without being limited by the capacity of an enclosure. In a continuous culture, water with nutrients and gases is continuously allowed into the growth enclosure to replenish the culture, and excess water is continuously removed while the algae in the water are harvested. The culture in the growth enclosure is maintained at a particular range of algal density or growth rate. In a semi-continuous culture, growing algae in an enclosure is harvested periodically followed by replenishment to about the original volume of water and concentrations of nutrient and gases. Preferably, the water in the system is recycled to the bivalves enclosure. In a preferred embodiment, the algae culture is a continuous culture, maintained in open air.

Most natural freshwater sources (rivers, lakes, springs) and municipal water supply can be used as a source of water for used in the systems provided herein. Seawater, saline, and brackish water from inland, coastal or estuarine regions, irrigation water, agricultural wastewater, industrial wastewater, or municipal wastewater can also be used in the systems provided herein. Depending on the source of water, it may be necessary to provide additional nutrients if the source is oligotrophic. In some embodiments, the source of water is eutrophic, in which case, the water comprises a plurality of algae, planktonic animals, and bacteria, and certain nutrients. Algae from the water can be used to inoculate the growth enclosure. Zooplankton that consumes algae can be removed by filtration or by flowing the water through an enclosure comprising zooplantivorous fishes.

The water for growing algae can comprise carbon dioxide, either dissolved or as bubbles, at a concentration from about 0.05% to 1% and up to 5% volume of the air introduced into the culture. The addition of carbon dioxide promotes photosynthesis, and helps to maintain the pH of the culture below pH 9. Sources of carbon dioxide include, but is not limited to, synthetic fuel plants, gasification power plants, oil recovery plants, ammonia plants, ethanol plants, oil refinery plants, anaerobic digestion units, cement plants, and fossil steam plants. The use of such carbon source in the culturing process enables carbon capture by the methods provided herein. For example, the water can be supplemented with fly ashes collected from gaseous output of coal-burning power generation plants. The chemical composition of fly ashes depends on the source, e.g., anthracite, bituminous, and lignite coal. Fly ashes range in size from 0.5 $\mu$m to 100 $\mu$m, and comprise silicon dioxide, calcium oxide, iron oxide, aluminum oxide. Silicon is required for the growth of algae, such as the diatoms. However, according to certain embodiments provided herein, the amount of carbon dioxide required to be added to the algae culture can be reduced by the presence of a population of growing bivalves. The growth enclosures can also be fertilized regularly according to conventional practices. Nutrients can be provided in the form of fertilizers, including inorganic fertilizers, such as but not limited to, ammonium sulfate, urea, calcium superphosphate, and various N/P/K fertilizers (16:20:20, or 14:14:14); such as but not limited to, manure and agricultural waste. Less fertilizer is required in the systems provided herein than a system without bivalves because the bivalves excrete dissolved and solid metabolic waste in the bivalves enclosure.

Means for culturing bivalves, algae and fishes are installed in the bivalves enclosure, the growth enclosures, and the fish enclosures, and generally include equipment to monitor and adjust the pH, salinity, temperature and/or dissolved gas in the water. The pH of the water is preferably kept within the ranges of from about pH6.5 to pH9, and more preferably from about 8.2 to about 8.7. The salinity of seawater ranges preferably from about 12 to about 40 g/L and more preferably from 20 to 24 g/L. The temperature for seawater-based culture ranges preferably from about 16° C. to about 27° C. or from about 18° C. to about 24° C.

According to the methods provided herein, a starter culture of algae can be used to seed a growth enclosure. A starter culture can also be used to inoculate a growth enclosure periodically to maintain a stable population of the desired species. The starter culture is grown in water enclosures typically smaller than the growth enclosure, referred to herein as "inoculation enclosures." The inoculation enclosures can be, but not limited to, one or more flasks, carboys, cylinders, plastic bags, chambers, indoor tanks, outdoor tanks, indoor ponds, and outdoor ponds, or a combination thereof. One or more inoculation enclosures can be temporarily or permanently connected to one or more growth enclosures and to each other with means for regulating fluid flow and flow direction, e.g., gate, valve. Typically, the volume of an inoculation enclosure ranges from 1 to 10 liters, 5 to 50 liters, 25 to 150 liters, 100 to 500 liters. In certain embodiments, the inoculation enclosure does not comprise fish.

For productive growth in an enclosure, the algae are exposed to light of an intensity that ranges from 1000 to 10,000 lux, preferably 2500 to 5000 lux. The photoperiod (light: dark in number of hours) ranges from about 12:12, about 14:10, about 16:8, about 18:6, about 20:4, about 22:2, and up to 24:0. The light intensity and photoperiod depend on the geographic location of the growth enclosures and the season, and may be manipulated by artificial illumination or shading. Mixing of water in the growth enclosure ensures that all algal cells are equally exposed to light and nutrients. Mixing is also necessary to prevent sedimentation of the algae to the bottom or to a depth where light penetration becomes limiting. Mixing also prevent thermal stratification of outdoor cultures. Mixing can be provided in part by the siphoning action of bivalves or by the presence of swimming fish in the growth enclosure. Where additional mixing is required, it can be provided by any means, mechanical or otherwise, including but not limited to, paddle wheels and jet pumps.

Means and techniques for bivalves culture are well known in the art and can be adapted to for use in certain embodiments provided herein without undue experimentation. For example, the bottom technique involves scattering on the bottom of the water spat-laden cultch. Stake culture involves attaching spat-laden shells to bamboo, wooden, cement, or PVC pipe stakes and driving the stakes into the bottom or laid out horizontally. Spat may be allowed to settle directly on the stakes. This technique is particularly useful in areas with soft bottoms that would not allow bottom culture. Umbrella culture uses bivalves that have been attached to ropes and suspended from a central post radiating to anchors like spokes on a wheel, thus taking the shape of an umbrella. Rack culture is accomplished by constructing racks of treated lumber, steel rebar, or concrete blocks. Ropes, sticks, or nylon mesh bags with bivalves attached or contained are placed on the racks for growout. The mesh bag technique is used quite extensively in areas that are too shallow for raft culture and too soft for bottom culture. Raft culture incorporates floating structures to suspend bivalves off the bottom. The rafts can be made of logs, bamboo, Styrofoam, or 55-gallon drums. Raft materials are lashed together to allow flexing with wave action. Rafts are anchored to the bottom securely. Strings, ropes, nets (pearl nets, lantern nets), trays, and bags of bivalves are suspended below the raft. The long line technique also involves suspending bivalves off the bottom, wherein spat-laden cultch are attached to polypropylene rope and strung between wooden, metal, or PVC plastic stakes inserted into the substrate. Other techniques known in the art can also be applied, see, for example, U.S. Pat. Nos. 3,811,411, 4,896,626, 5,511,514 and 5,836,266. The bivalves can be fed with algae produced in the growth enclosure by flowing an effluent from the growth enclosure. The amount of algae allowed to flow into the bivalves enclosure is monitored and controlled so that the yield of the system is not affected by over-consumption by the bivalves. The amount of algae can be controlled by adjusting the flow rate of the effluent, the concentration of algae in the effluent, or the amount of time that the flow is established. In addition, the bivalves can also be fed with algae present in the source of the water, or the residual algae that are not consumed by planktivorous fishes provided herein.

In addition to algae and bivalves, the bivalves and growth enclosure may comprise other aquatic life, such as fishes, bacteria, zooplankton, aquatic plants, insects, worms, and nematodes. These bacteria, plants, and animals constitute various trophic levels of an ecological system and lend stability to an algal culture grown in an open pond. However, zooplankton grazing on microalgae compete with bivalves for food and are generally undesirable in the growth enclosure. They can be removed from the water by sand filtration or controlled by keeping zooplanktivorous fishes in an enclosure. The numbers and species of planktons, including zooplanktons, can be assessed by counting under a microscope using, for example, a Sedgwick-Rafter cell.

In various embodiments, the algae are concentrated so that the number of algal cells per unit volume increases by two, five, 10, 20, 25, 30, 40, 50, 75, 100-fold, or more. For example, the starting concentration of an algal culture can range from about 0.05 g/L, about 0.1 g/L, about 0.2 g/L, about 0.5 g/L to about 1.0 g/L. After the concentration step, the concentration of algae in an algal composition can range from at least about 0.2 g/L, about 0.5 g/L, about 1.0 g/L, about 2.0 g/L, about 5 g/L to about 10 g/L. An alternative system to assess algal concentration that measures chlorophyll-a concentration ($\mu$g/L) can be used similarly. The concentration of algae can be increased progressively by concentrating the algae in multiple stages. Starting in the growth enclosure, the algal culture is concentrated to provide an algal composition comprising algae at a density or concentration that is higher than that of the algal culture in the growth enclosure. The concentrated algal composition can be subjected to another round of concentration using the same or a different technique. Although it is desirable to remove as much water as possible from the algae before processing, it should be understood that the concentration step does not require that the algae be dried, dewatered, or reduced to a paste or any semi-solid state. The resulting concentrated algae composition can be a solid, a semi-solid (e.g., paste), or a liquid (e.g., a suspension). It can be stored for future use, used to make biofuel, or used as feed for the bivalves.

The choice of fish for use in the harvesting methods provided herein depends on a number of factors, such as the palatability and nutritional value of the cultured algae as food for the fishes, the lipid composition and content of the fish, the feed conversion ratio, the fish growth rate, and the environmental requirements that encourages feeding and growth of the fish. For example, it is preferable that the selected fishes will feed on the cultured algae until satiation, and convert the algal biomass into fish biomass rapidly and efficiently. Gut content analysis can reveal the dimensions of the plankton ingested by the planktivore and the preference of the planktivore for certain species of algae. Knowing the average dimensions of ingested plankton, the preference and efficiency of the planktivore towards a certain size class of plankton can be determined. The size preference of a planktivore can be used to match the dimensions of algae in the algal composition to improve efficiency, e.g., sizes of algae being greater than about 20 μm, about 20-200 μm. It may also be preferable to deploy combinations of algae and fishes that are parts of a naturally occurring trophic system. Many trophic systems are known in the art and can be used to guide the selection of algae and fishes for use in certain embodiments provided herein.

The selected fishes should grow well in water of a salinity which is similar to that of the algal culture, so as to reduce the need to change water when the algae is brought to the fishes. For an open pond system, it may be preferable to use endemic species of fishes. Fishes from different taxonomic groups can be used in the growth enclosure or fish enclosure. It should be understood that, in various embodiments, fishes within a taxonomic group, such as a family or a genus, can be used interchangeably in various methods provided herein. Certain embodiments provided herein described below using common names of fish groups and fishes, as well as the scientific names of exemplary species. Databases, such as FishBase by Froese, R. and D. Pauly (Ed.), World Wide Web electronic publication, www.fishbase.org, version (06/2008), provide additional useful fish species within each of the taxonomic groups that are useful in certain embodiments provided herein. It is contemplated that one of ordinary skill in art could, consistent with the scope of certain embodiments provided herein, use the databases to specify other species within each of the described taxonomic groups for use in the methods provided herein.

In certain embodiments, the fishes used comprise fishes in the order Clupeiformes, i.e., the clupeids, which include the following families: Chirocentridae, Clupeidae (menhadens, shads, herrings, sardines, hilsa), Denticipitidae, Engraulidae (anchovies). Exemplary members within the order Clupeiformes include but not limited to, the menhadens (*Brevoortia* species), e.g., *Ethmidium maculatum, Brevoortia aurea, Brevoortia gunteri, Brevoortia smithi, Brevoortia pectinata,* Gulf menhaden (*Brevoortia patronus*), and Atlantic menhaden (*Brevoortia tyrannus*); the shads, e.g., *Alosa alosa, Alosa alabamae, Alosa fallax, Alosa mediocris, Alosa sapidissima, Alos pseudoharengus, Alosa chrysochloris, Dorosoma petenense*; the herrings, e.g., *Etrumeus teres, Harengula thrissina,* Pacific herring (*Clupea pallasii pallasii*), *Alosa aestivalis, Ilisha africana, Ilisha elongata, Ilisha megaloptera, Ilisha melastoma, Ilisha pristigastroides, Pellona ditchela, Opisthopterus tardoore, Nematalosa come, Alosa aestivalis, Alosa chrysochloris,* freshwater herring (*Alosa pseudoharengus*), *Arripis georgianus, Alosa chrysochloris, Opisthonema libertate, Opisthonema oglinum,* Atlantic herring (*Clupea harengus*), Baltic herring (*Clupea harengus membras*); the sardines, e.g., *Ilisha* species, *Sardinella* species, *Amblygaster* species, *Opisthopterus equatorialis, Sardinella aurita,* Pacific sardine (*Sardinops sagax*), *Harengula clupeola, Harengula humeralis, Harengula thrissina, Harengulajaguana, Sardinella albella, Sardinella janeiro, Sardinella fimbriata,* oil sardine (*Sardinella longiceps*), and European pilchard (*Sardina pilchardus*); the hilsas, e.g., *Tenuolosa* species, and the anchovies, e.g., *Anchoa* species (*A. hepsetus, A. mitchillis*), *Engraulis* species, *Thryssa* species, anchoveta (*Engraulis ringens*), European anchovy (*Engraulis encrasicolus*), *Engraulis eurystole,* Australian anchovy (*Engraulis australis*), and *Setipinna phasa, Coilia dussumieri*.

In a preferred embodiment, the fishes used are shiners. A variety of shiners that inhabit the Gulf of Mexico, particularly Northern Gulf of Mexico, can be used. Examples of shiners include but are not limited to, members of *Luxilus, Cyprinella* and *Notropis* genus, Alabama shiner (*Cyprinella callistia*), Altamaha shiner (*Cyprinella xaenura*), Ameca shiner (*Notropis amecae*), Ameca shiner (*Notropis amecae*), Apalachee shiner (*Pteronotropis grandipinnis*), Arkansas River shiner (*Notropis girardi*), Aztec shiner (*Aztecula sallaei old*), Balsas shiner (*Hybopsis boucardi*), Bandfin shiner (*Luxilus zonistius*), Bannerfin shiner (*Cyprinella leedsi*), Beautiful shiner (*Cyprinella formosa*), Bedrock shiner (*Notropis rupestris*), Bigeye shiner (*Notropis boops*), Bigmouth shiner (*Hybopsis dorsalis*), Blackchin shiner (*Notropis heterodon*), Blackmouth Shiner (*Notropis melanostomus*), Blacknose shiner (*Can Quebec Notropis heterolepis*), Blacknose shiner (*Notropis heterolepis*), Blackspot shiner (*Notropis atrocaudalis*), Blacktail shiner (*Cyprinella venusta*), Blacktip shiner (*Lythrurus atrapiculus*), Bleeding shiner (*Luxilus zonatus*), Blue Shiner (*Cyprinella caerulea*), Bluehead Shiner (*Pteronotropis hubbsi*), Bluenose Shiner (*Pteronotropis welaka*), Bluestripe Shiner (*Cyprinella callitaenia*), Bluntface shiner (*Cyprinella camura*), Bluntnose shiner (*Notropis simus*), Bluntnosed shiner (*Selene setapinnis*), Bridle shiner (*Notropis bifrenatus*), Broadstripe shiner (*Notropis euryzonus*), Burrhead shiner (*Notropis asperifrons*), Cahaba Shiner (*Notropis cahabae*), Cape Fear Shiner (*Notropis mekistocholas*), Cardinal shiner (*Luxilus cardinalis*), Carmine shiner (*Notropis percobromus*), Channel shiner (*Notropis wickliffi*), Chemyfin shiner (*Lythrurus roseipinnis*), Chihuahua shiner (*Notropis chihuahua*), Chub shiner (*Notropis potteri*), Coastal shiner (*Notropis petersoni*), Colorless Shiner (*Notropis perpallidus*), Comely shiner (*Notropis amoenus*), Common emerald shiner (*Notropis atherinoides*), Common shiner (*Luxilus cornutus*), Conchos shiner (*Cyprinella panarcys*), Coosa shiner (*Notropis xaenocephalus*), Crescent shiner (*Luxilus cerasinus*), Cuatro Cienegas shiner (*Cyprinella xanthicara*), Durango shiner (*Notropis aulidion*), Dusky shiner (*Notropis cummingsae*), Duskystripe shiner (*Luxilus pilsbryi*), Edwards Plateau shiner (*Cyprinella lepida*), Emerald shiner (*Notropis atherinoides*), Fieryblack shiner (*Cyprinella pyrrhomelas*), Flagfin shiner (*Notropis signipinnis*), Fluvial shiner (*Notropis edwardraneyi*), Ghost shiner (*Notropis buchanani*), Gibbous shiner (*Cyprinella garmani*), Golden shiner (*Notemigonus crysoleucas*), Golden shiner minnow (*Notemigonus crysoleucas*), Greenfin shiner (*Cyprinella chloristia*), Greenhead shiner (*Notropis chlorocephalus*), Highfin shiner (*Notropis altipinnis*), Highland shiner (*Notropis micropteryx*), Highscale shiner (*Notropis hypsilepis*), Ironcolor shiner (*Notropis chalybaeus*), Kiamichi shiner (*Notropis ortenburgeri*), Lake emerald shiner (*Notropis atherinoides*), Lake shiner (*Notropis atherinoides*), Largemouth shiner (*Cyprinella bocagrande*), Longnose shiner (*Notropis longirostris*), Mexican red shiner (*Cyprinella rutila*), Mimic shiner (*Notropis volucellus*), Mirror shiner (*Notropis spectrunculus*), Mountain shiner (*Lythrurus lirus*), Nazas shiner (*Notropis nazas*), New River shiner (*Notropis scabriceps*), Ocmulgee shiner (*Cyprinella callisema*), Orangefin shiner (*Notropis ammophilus*), Orangetail shiner (*Pteronotropis merlini*), Ornate shiner (*Cyprinella ornata*), Ouachita Mountain Shiner (*Lythrurus snelsoni*), Ouachita shiner (*Lythrurus snelsoni*), Ozark shiner (*Notropis ozarcanus*), Paleband shiner (*Notropis albizonatus*), Pallid shiner (*Hybopsis amnis*), Peppered shiner (*Notropis perpallidus*), Phantom shiner (*Notropis orca*), Pinewoods shiner (*Lythrurus matutinus*), Plateau shiner (*Cyprinella lepida*), Popeye shiner (*Notropis ariommus*), Pretty shiner (*Lythrurus bellus*), Proserpine shiner (*Cyprinella proserpina*), Pugnose shiner (*Notropis anogenus*), Pygmy shiner (*Notropis tropicus*), Rainbow shiner (*Notropis chrosomus*), Red River shiner (*Notropis bairdi*), Red shiner (*Cyprinella lutrensis*), Redfin shiner (*Lythrurus umbratilis*), Redlip shiner (*Notropis chiliticus*), Redside shiner (*Richardsonius balteatus*), Ribbon shiner (*Lythrurus fumeus*), Rio Grande bluntnose shiner (*Notropis simus*), Rio Grande shiner (*Notropis jemezanus*), River shiner (*Notropis blennius*), Rocky shiner (*Notropis suttkusi*), Rosefin shiner (*Lythrurus ardens*), Rosyface shiner (*Notropis rubellus*), Rough shiner (*Notropis baileyi*), Roughhead Shiner (*Notropis semperasper*), Sabine shiner (*Notropis sabinae*), Saffron shiner (*Notropis rubricroceus*), Sailfin shiner (*Notropis hypselopterus*), Salado shiner (*Notropis saladonis*), Sand shiner (*Notropis stramineus*), Sandbar shiner (*Notropis scepticus*), Satinfin shiner (*Cyprinella analostana*), Scarlet shiner (*Lythrurus fasciolaris*), Sharpnose Shiner (*Notropis oxyrhynchus*), *Notropis atherinoides*, *Notropis hudsonius*, *Richardsonius balteatus*, *Pomoxis nigromaculatus*, *Cymatogaster aggregata*, Shiner Mauritania (*Selene dorsalis*), Silver shiner (*Notropis photogenis*), Silver shiner (*Richardsonius balteatus*), Silver shiner (*Richardsonius balteatus*), Silver shiner (*Notropis photogenis*), Silverband shiner (*Notropis shumardi*), Silverside shiner (*Notropis candidus*), Silverstripe shiner (*Notropis stilbius*), Skygazer shiner (*Notropis uranoscopus*), Smalleye Shiner (*Notropis buccula*), Soto la Marina shiner (*Notropis aguirrepequenoi*), Spotfin shiner (*Cyprinella spiloptera*), Spottail shiner (*Notropis hudsonius*), Steelcolor shiner (*Cyprinella whipplei*), Striped shiner (*Luxilus chrysocephalus*), Swallowtail shiner (*Notropis procne*), Taillight shiner (*Notropis maculatus*), Tallapoosa shiner (*Cyprinella gibbsi*), Tamaulipas shiner (*Notropis braytoni*), Telescope shiner (*Notropis telescopus*), Tennessee shiner (*Notropis leuciodus*), Tepehuan shiner (*Cyprinella alvarezdelvillari*), Texas shiner (*Notropis amabilis*), Topeka shiner (*Notropis topeka*), Tricolor shiner (*Cyprinella trichroistia*), Turquoise Shiner (*Erimonax monachus*), Warpaint shiner (*Luxilus coccogenis*), Warrior shiner (*Lythrurus alegnotus*), Wedgespot shiner (*Notropis greenei*), Weed shiner (*Notropis texanus*), White shiner (*Luxilus albeolus*), Whitefin shiner (*Cyprinella nivea*), Whitemouth shiner (*Notropis alborus*), Whitetail shiner (*Cyprinella galactura*), Yazoo shiner (*Notropis rafinesquei*), Yellow shiner (*Cymatogaster aggregata*), Yellow shiner (*Notropis calientis*), and Yellowfin shiner (*Notropis lutipinnis*).

Other exemplary fish species that can be used to harvest algae include: *Brevoortia* species such as *B. patronus* and *B. tyrannus*, *Hyporhamphus unifasciatus*, *Sardinella aurita*, *Adinia xenica*, *Diplodus holbrooki*, *Dorosoma petenense*, *Lagodon rhombodides*, *Microgobius gulosus*, *Mugil* species such as *Mugil cephalus*, *Mugil cephalus*, *Mugil curema*, *Sphoeroides* species such as *Sphoeroides maculatus*, *Sphoeroides nephelus*, *Sphoeroides parvus*, *Sphoeroides spengleri*, *Aluterus schoepfi*, *Anguilla rostrata*, *Arius felis*, *Bairdella chrysoura*, *Bairdeiella chrysoura*, *Chasmodies* species such as *Chasmodes saburrae* and *Chasmodies saburrae*, *Diplodus holbrooki*, *Heterandria formosa*, *Hybopsis winchelli*, *Ictalurus* species such as *Ictalurus serracantus* and *Ictalurus punctatus*, *Leiostomus xanthurus*, *Micropogonias undulatus*, *Monacanthus ciliatus*, *Notropis texanus*, *Opisthonema oglinum*, *Orthopristis chrysoptera*, *Stephanolepis hispidus*, *Syndousfoetens*, *Syngnathus* species such as *Syngnathus scovelli*, *Trinectes maculatus*, *Archosargus probatocephalus*, *Carpiodes* species such as *C. cyprinus* and *C. velifer*, *Dorosoma cepedianum*, *Erimyzon* species such as *Erimyzon oblongus*, *Erimyzon sucetta*, and *Erimyzon tenuis*, *Floridichthys carpio*, *Microgobius gulosus*, *Monacanthus cilatus*, *Moxostoma poecilurum*, and *Orthopristis chrysophtera*.

Transgenic fish and genetically improved fish can also be used in the culturing and/or harvesting methods provided herein. The term "genetically improved fish" refers herein to a fish that is genetically predisposed to having a higher growth rate and/or a lipid content that is higher than a wild type fish, when they are cultured under the same conditions. Such fishes can be obtained by traditional breeding techniques or by transgenic technology. Over-expression or ectopic expression of a piscine growth hormone transgene in a variety of fishes resulted in enhanced growth rate. For example, the growth hormone genes of Chinook salmon, Sockeye salmon, Tilapia, Atlantic salmon, grass carp, and mud loach have been used in creating transgenic fishes (Zbikowska, Transgenic Research, 12:379-389, 2003; Guan et al., Aquaculture, 284:217-223, 2008). Transgenic carp or transgenic tilapia comprising an ectopically-expressed piscine growth hormone transgene are particularly useful in the harvesting methods provided herein.

Examples of means and methods for processing lipids such as algal oil and fish lipids into biofuel, such as biodiesel, can be found in the following patent publications, the entire contents of each of which are incorporated by reference herein: U.S. Patent Publication No. 2007/0010682, entitled "Process for the Manufacture of Diesel Range Hydrocarbons;" U.S. Patent Publication No. 2007/0131579, entitled "Process for Producing a Saturated Hydrocarbon Component;" U.S. Patent Publication No. 2007/0135316, entitled "Process for Producing a Saturated Hydrocarbon Component;" U.S. Patent Publication No. 2007/0135663, entitled "Base Oil;" U.S. Patent Publication No. 2007/0135666, entitled "Process for Producing a Branched Hydrocarbon Component;" U.S. Patent Publication No. 2007/0135669, entitled "Process for Producing a Hydrocarbon Component;" and U.S. Patent Publication No. 2007/0299291, entitled "Process for the Manufacture of Base Oil."

In certain embodiments, the extraction of lipids from the fishes can comprise heating the fish to a temperature between 70° C. to 100° C., pressing the fishes to release the lipids, and collecting the lipids. Separation of the lipids from an aqueous phase and/or a solid phase can be included in the extraction step. The entire fish or a portion thereof can be used to extract lipids. If lipid concentrates are desired, several established methods could be employed, including chromatography, fractional or molecular distillation, enzymatic splitting, low-temperature crystallization, supercritical fluid extraction, or urea complexation.

In certain embodiments, the processing step involves heating the fishes to greater than about 70° C., 80° C., 90° C. or 100° C., typically by a steam cooker, which coagulates the protein, ruptures the fat deposits and liberates lipids and oil and physico-chemically bound water, and; grinding, pureeing and/or pressing the fish by a continuous press with rotating helical screws. The fishes can be subjected to gentle pressure cooking and pressing which use significantly less energy than that is required to obtain lipids from algae. The coagulate may alternatively be centrifuged. This step removes a large fraction of the liquids (press liquor) from the mass, which comprises an oily phase and an aqueous fraction (stickwater). The separation of press liquor can be carried out by centrifugation after the liquor has been heated to 90° C. to 95° C. Separation of stickwater from oil can be carried out in vertical disc centrifuges. The lipids in the oily phase (fish oil) may be polished by treating with hot water which extracts impurities from the lipids.

In certain embodiments, the extracted fish lipids are not limited to use as biofuels. In one embodiment, the extracted fish lipids can be used to obtain omega 3 fatty acids, such as eicosahexaenoic acid (EPA) and/or docosahexaenoic acid (DHA) and/or derivatives thereof including, but not limited to esters, glycerides, phospholipids, sterols, and/or mixtures thereof. In one embodiment, the extracted fish lipids contain EPA and/or DHA ranging from 1 to 50%, depending on the fish species, age, location, and a host of ecological and environmental factors. If higher EPA and/or DHA concentrations are desired, several established methods could be employed, including chromatography, fractional or molecular distillation, enzymatic splitting, low-temperature crystallization, supercritical fluid extraction, or urea complexation. These methods can further concentrate the EPA and/or DHA to nearly pure EPA and/or DHA.

In certain embodiments, EPA- and/or DHA-containing lipids may be separated and concentrated by short-path distillation, or molecular distillation. The lipids are first transesterified, either acid- or base-catalyzed, with ethanol to produce a mixture of fatty acid ethyl esters (FAEE). The FAEE are then fractionated in the short-path distillation to remove the short chain FAEE, C-14 to C-18. The concentrate of FAEE from C-20 to C-22 is where the EPA and/or DHA can be found. A second distillation of the concentrate can result in a final Omega-3 content of up to 70%. The concentration of the EPA and/or DHA in the final product will depend on the initial lipid profile of the fish oil. The FAEE can be used as a consumer product at this stage (fish oil capsules). In some countries, the FAEE are required to be reconverted to triglycerides through a glycerolysis reaction before they can be sold as a consumer product. In order to obtain pure EPA and/or DHA, an additional purification step is required using chromatography, enzymatic transesterification, ammonia complexation, or supercritical fluid extraction.

All references cited herein are incorporated herein by reference in their entirety and for all purposes to the same extent as if each individual publication or patent or patent application was specifically and individually indicated to be incorporated by reference in its entirety for all purposes.

Many modifications and variations of this invention can be made without departing from its spirit and scope, as will be apparent to those skilled in the art. The specific embodiments described herein are offered by way of example only, and the invention is to be limited only by the terms of the appended claims along with the full scope of equivalents to which such claims are entitled.

What is claimed:

1. A method for producing biofuel comprising
   (i) providing a source of water and a system comprising enclosures and water for culturing algae, culturing planktivorous fishes, and culturing bivalves,
   (ii) culturing the bivalves that increase the level of at least one dissolved nutrient in the water in the system relative to the water from the source;
   (iii) culturing the algae in the water in the system;
   (iv) culturing the planktivorous fishes in the water in the system;
   (v) feeding the algae to the bivalves at a rate such that the amount of algae produced in the system is greater than when the algae is cultured in the system without the bivalves;
   (vi) harvesting the algae by feeding the algae to the planktivorous fishes;
   (vii) harvesting the planktivorous fishes;
   (viii) extracting lipids from the harvested planktivorous fishes; and
   (ix) polishing the lipids to form biofuel.

2. The method of claim 1, wherein the bivalves are cultured in a bivalves enclosure separately from the algae cultured in a growth enclosure;
   the step of culturing the algae comprises flowing an effluent from the bivalves enclosure to the growth enclosure, said effluent from the bivalves enclosure having a level of at least one dissolved nutrient that is increased relative to the water from the source; and
   the step of culturing the bivalves comprises recirculating an effluent from the growth enclosure to the bivalves enclosure.

3. The method of claim 1, wherein the bivalves are cultured in a bivalves enclosure separately from the algae cultured in a growth enclosure;
   the fishes are cultured in a fish enclosure separately from the bivalves or the algae;
   the step of culturing the algae comprises flowing an effluent from the bivalves enclosure to the growth enclosure, said effluent from the bivalves enclosure having a level of at least one dissolved inorganic nutrient that is increased relative to the water from the source; and
   the step of culturing the bivalves comprises flowing an effluent from the growth enclosure to the bivalves enclosure and flowing an effluent from the fish enclosure to the bivalves enclosure.

4. The method of claim 3, wherein the step of culturing the bivalves comprises flowing the effluent from the fish enclosure to the bivalves enclosure at a rate effective for the bivalves to feed on residual plankton in the effluent from the fish enclosure, as indicated by a lower number of plankton in the effluent from the bivalves enclosure than the number of plankton in the effluent from the fish enclosure.

5. The method of claim 1, further comprising flowing water from the source into the bivalves enclosure prior to the growth enclosure, such that the level of at least one dissolved inorganic nutrient is increased relative to the water from the source.

6. The method of claim 5, further comprising removing zooplankton in water from the source prior to flowing the water from the source into the bivalves enclosure.

7. The method of claim 1, wherein the dissolved nutrient is carbon dioxide, ammonia, ammonium ion, a nitrite, nitrite ion, a nitrate, nitrate ion, a phosphate, or orthophosphate ion.

8. The method of claim 1, wherein the bivalves are *Mytilus edulis* and/or *Crassostrea virginica*.

9. The method of claim 1, wherein the planktivorous fishes are *Brevoortia patronus* and/or *Clupea harengus*.

10. A method for producing biofuel comprising
    (i) providing a source of water and a system comprising enclosures and water for culturing algae, culturing planktivorous fishes, and culturing bivalves,
    (ii) culturing the bivalves that increase the level of at least one dissolved nutrient in the water in the system relative to the water from the source;
    (iii) culturing the algae in the water in the system;
    (iv) culturing the planktivorous fishes in the water in the system;
    (v) feeding the algae to the bivalves at a rate such that the amount of algae produced in the system is greater than when the algae is cultured in the system without the bivalves;
    (vi) harvesting the algae by feeding the algae to the planktivorous fishes;
    (vii) harvesting the planktivorous fishes; and
    (viii) extracting lipids from the harvested planktivorous fishes.

11. The method of claim 10, wherein the bivalves are cultured in a bivalves enclosure separately from the algae cultured in a growth enclosure;
    the step of culturing the algae comprises flowing an effluent from the bivalves enclosure to the growth enclosure, said effluent from the bivalves enclosure having a level of at least one dissolved nutrient that is increased relative to the water from the source; and the step of culturing the bivalves comprises recirculating an effluent from the growth enclosure to the bivalves enclosure.

12. The method of claim 10, wherein the bivalves are cultured in a bivalves enclosure separately from the algae cultured in a growth enclosure;

the fishes are cultured in a fish enclosure separately from the bivalves or the algae;

the step of culturing the algae comprises flowing an effluent from the bivalves enclosure to the growth enclosure, said effluent from the bivalves enclosure having a level of at least one dissolved inorganic nutrient that is increased relative to the water from the source; and the step of culturing the bivalves comprises flowing an effluent from the growth enclosure to the bivalves enclosure and flowing an effluent from the fish enclosure to the bivalves enclosure.

13. The method of claim 10, wherein the step of culturing the bivalves comprises flowing the effluent from the fish enclosure to the bivalves enclosure at a rate effective for the bivalves to feed on residual plankton in the effluent from the fish enclosure, as indicated by a lower number of plankton in the effluent from the bivalves enclosure than the number of plankton in the effluent from the fish enclosure.

14. The method of claim 10, further comprising flowing water from the source into the bivalves enclosure prior to the growth enclosure, such that the level of at least one dissolved inorganic nutrient is increased relative to the water from the source.

15. The method of claim 14, further comprising removing zooplankton in water from the source prior to flowing the water from the source into the bivalves enclosure.

16. The method of claim 10, wherein the dissolved nutrient is carbon dioxide, ammonia, ammonium ion, a nitrite, nitrite ion, a nitrate, nitrate ion, a phosphate, or orthophosphate ion.

17. The method of claim 10, wherein the bivalves are *Illytilus edulis* and/or *Crassostrea virginica*.

18. The method of claim 10, wherein the planktivorous fishes are *Brevoortia patronus* and/or *Clupea harengus*.

19. The method of claim 10, further comprising processing the lipids to form EPA- and/or DHA-containing products for human consumption or animal feeds.

20. The method of claim 10, wherein said extracting step comprises a processing technique selected from chromatography, fractional or molecular distillation, enzymatic splitting, low-temperature crystallization, supercritical fluid extraction, or urea complexation.

21. A system for producing biofuel comprising
(i) a source of water;
(ii) a growth enclosure for culturing algae, a fish enclosure for culturing planktivorous fishes, and a bivalves enclosure for culturing bivalves, wherein the growth enclosure, the fish enclosure, and the bivalves enclosure are each in fluid communication with the other enclosures;
(iii) means to regulate independently the rate, direction, or both the rate and direction, of fluid flow between each of the bivalves enclosure, the growth enclosure and the fish enclosure;
(iv) means for culturing the bivalves that increase the level of at least one dissolved inorganic nutrient in an effluent from the bivalves enclosure relative to the water from the source;
(v) means for culturing the algae in the effluent from the bivalves enclosure;
(vi) means for culturing the planktivorous fishes;
(vii) means for feeding a controlled amount of the algae to the bivalves such that the amount of algae produced in the system is greater than when the algae is cultured in the system without the bivalves;
(viii) means for harvesting the algae by the planktivorous fishes;
(ix) means for harvesting the planktivorous fishes; and
(x) means for extracting lipids from the harvested planktivorous.

22. The system of claim 21, further comprising
(xi) means for polishing the lipids to form biofuel.

* * * * *

UNITED STATES PATENT AND TRADEMARK OFFICE
CERTIFICATE OF CORRECTION

PATENT NO. : 8,753,851 B2
APPLICATION NO. : 13/263980
DATED : June 17, 2014
INVENTOR(S) : David Stephen et al.

Page 1 of 1

It is certified that error appears in the above-identified patent and that said Letters Patent is hereby corrected as shown below:

Title Page
Item (63), delete "Continuation of application No. 13/263,980, filed as application No. PCT/US2010/031340 on Apr. 16, 2010."

In the Specification
Column 1
Lines 4-6, delete the entire paragraph and substitute the following:

--This application is the National Stage of International Application No. PCT/US2010/031340, filed April 16, 2010, which claims the benefit of U.S. Provisional Application No. 61/170,524, filed April 17, 2009, each of which is incorporated by reference in its entirety.--

Signed and Sealed this
Ninth Day of September, 2014

Michelle K. Lee
*Deputy Director of the United States Patent and Trademark Office*